United States Patent [19]
Whittaker et al.

[11] Patent Number: 5,849,013
[45] Date of Patent: Dec. 15, 1998

[54] METHOD AND APPARATUS FOR FIXING A BONE BLOCK IN A BONE TUNNEL

[76] Inventors: Gregory R. Whittaker, 21 Rustic Rd., Stoneham, Mass. 02180; Harold M. Martins, 17 Scribner Park, Newton, Mass. 02166; Shawn T. Huxel, 3297 Ridge Way Rd., Lakehurst, N.J. 08733; Joan M. Sullivan, 61 Old Schoolhouse La., Hanover, Mass. 02339; Ronald L. Taylor, Jr., 62 Adams Ave., Everett, Mass. 02149

[21] Appl. No.: 783,627

[22] Filed: Jan. 14, 1997

[51] Int. Cl.⁶ .................................................. A61B 17/56
[52] U.S. Cl. ................... 606/72; 606/77; 606/79; 606/96
[58] Field of Search ................... 606/98, 96, 97, 606/73, 72, 77, 86, 80, 79

[56] References Cited

U.S. PATENT DOCUMENTS

| | | |
|---|---|---|
| 3,973,277 | 8/1976 | Semple et al. . |
| 4,858,603 | 8/1989 | Clemow et al. . |
| 4,898,156 | 2/1990 | Gatturna et al. . |
| 4,899,743 | 2/1990 | Nicholson et al. . |
| 4,901,711 | 2/1990 | Goble et al. ................ 606/98 |
| 4,944,742 | 7/1990 | Clemow et al. . |
| 4,950,270 | 8/1990 | Bowman et al. . |
| 4,968,315 | 11/1990 | Gatturna et al. . |
| 4,985,032 | 1/1991 | Goble ......................... 606/96 |
| 5,004,474 | 4/1991 | Fronk et al. . |
| 5,067,962 | 11/1991 | Campbell et al. . |
| 5,147,362 | 9/1992 | Goble . |
| 5,152,764 | 10/1992 | Goble ......................... 606/96 |
| 5,234,434 | 8/1993 | Goble et al. ................ 606/96 |
| 5,266,075 | 11/1993 | Clark et al. . |
| 5,350,380 | 9/1994 | Goble et al. . |
| 5,354,300 | 10/1994 | Goble et al. ................ 606/80 |
| 5,356,413 | 10/1994 | Martins et al. . |
| 5,356,435 | 10/1994 | Thein . |
| 5,364,400 | 11/1994 | Rego, Jr. et al. ........... 606/72 |
| 5,372,599 | 12/1994 | Martins . |
| 5,376,119 | 12/1994 | Zimmermann et al. . |
| 5,393,302 | 2/1995 | Clark et al. . |
| 5,397,356 | 3/1995 | Goble et al. . |
| 5,431,651 | 7/1995 | Goble ......................... 606/73 |
| 5,470,334 | 11/1995 | Ross et al. ................. 606/72 |
| 5,522,817 | 6/1996 | Sander et al. . |
| 5,688,284 | 11/1997 | Chervitz et al. ............ 606/96 |
| 5,697,933 | 12/1997 | Gundlapalli et al. ........ 606/96 |

*Primary Examiner*—Guy V. Tucker
*Attorney, Agent, or Firm*—Pandiscio & Pandiscio

[57] ABSTRACT

A method for fixing a bone block in a bone tunnel comprising the steps of placing the bone block in the bone tunnel, advancing spaced-apart first and second metal wires through the bone, transversely of the bone tunnel, so as to intersect the bone block and extend through the bone block, removing one of the wires and replacing the one removed wire with a first absorbable rod, and removing the other of the wires and replacing the other removed wire with a second absorbable rod, whereby to retain the bone block in the bone tunnel with the absorbable rods.

26 Claims, 34 Drawing Sheets

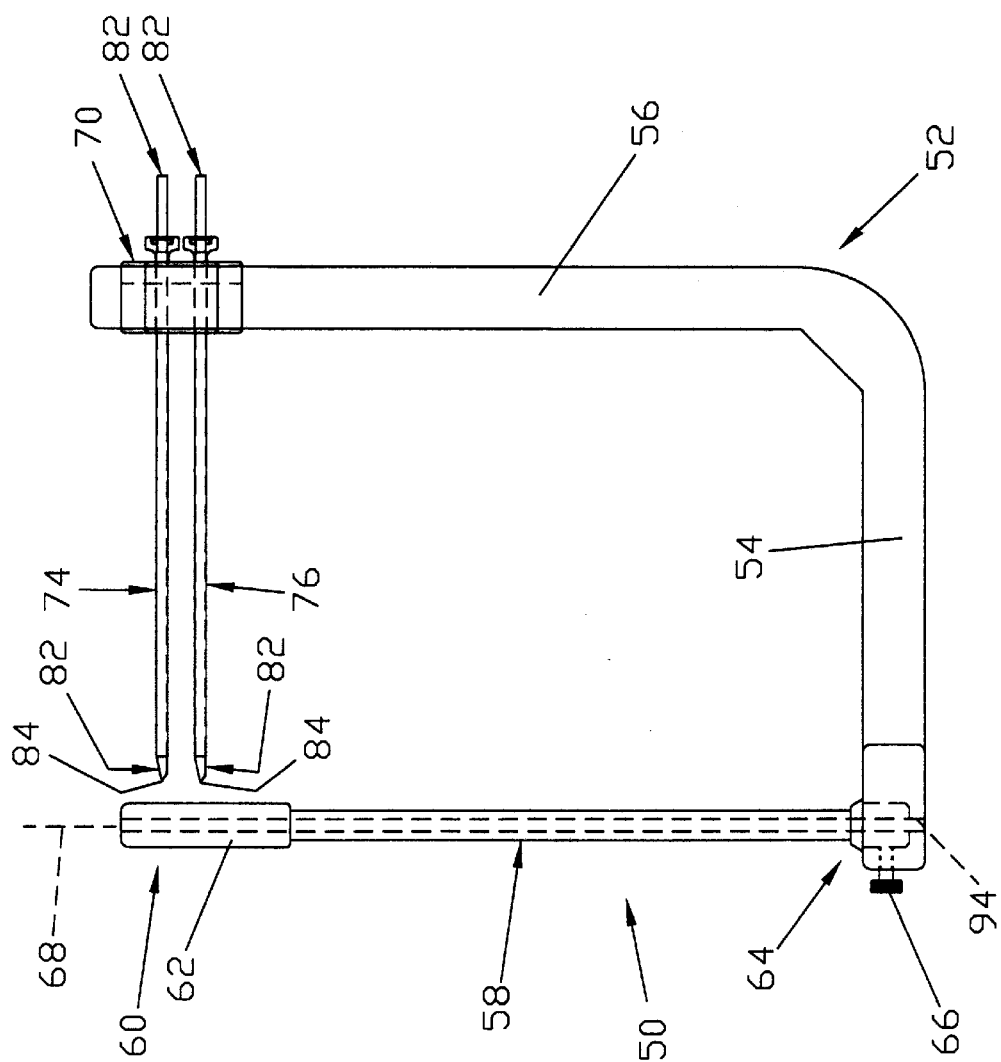

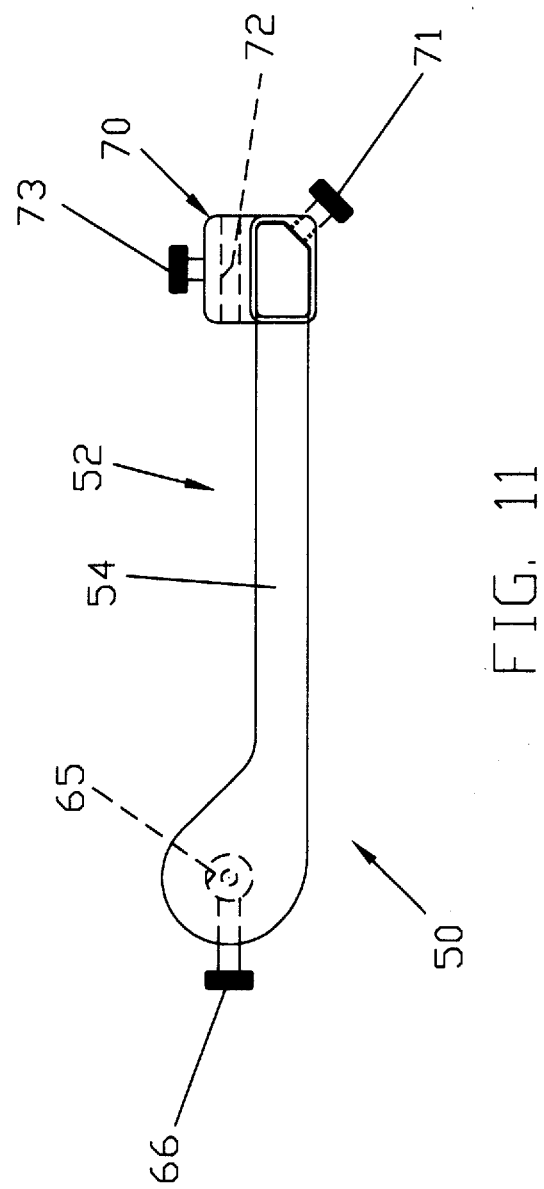

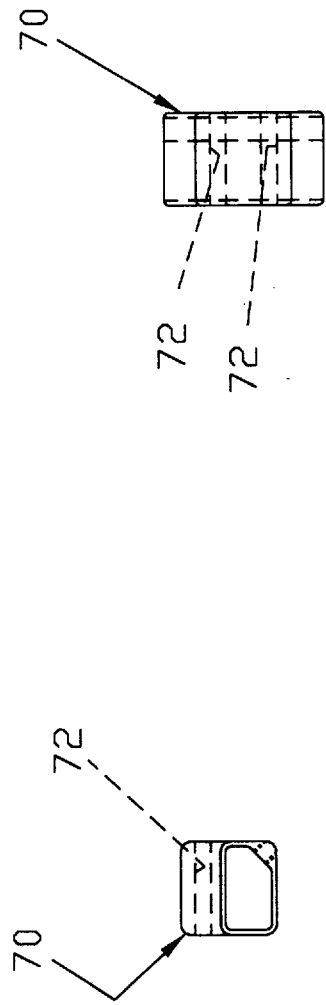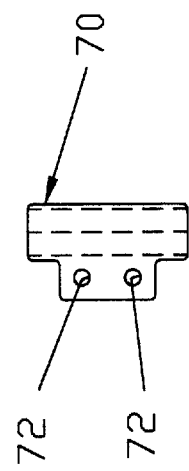
FIG. 13
FIG. 14
FIG. 12

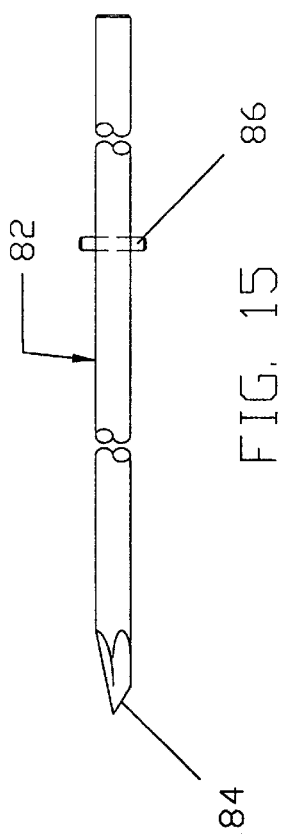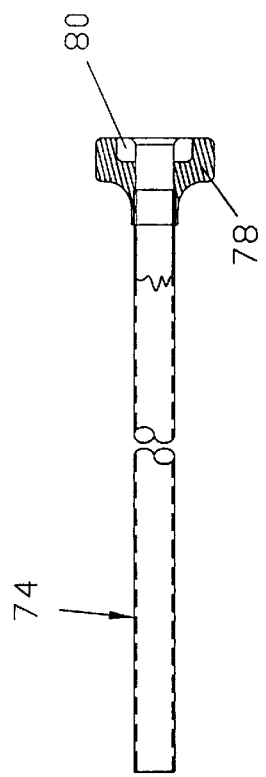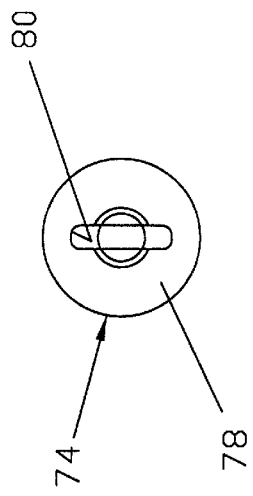

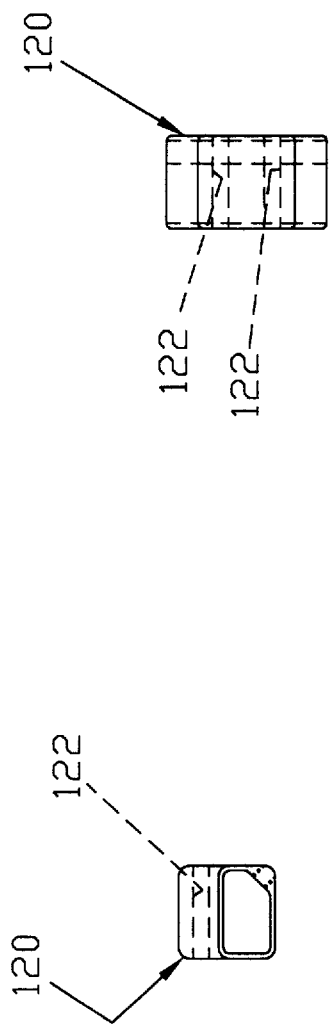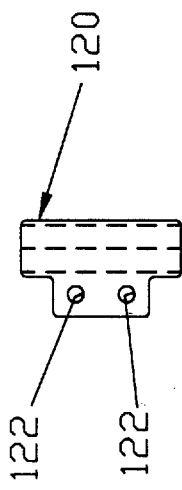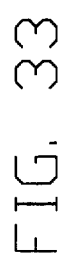
FIG. 31
FIG. 32
FIG. 33

METHOD AND APPARATUS FOR FIXING A BONE BLOCK IN A BONE TUNNEL

FIELD OF THE INVENTION

This invention relates to surgical methods and apparatus in general, and more particularly to methods and apparatus for fixing bone blocks in bone tunnels.

BACKGROUND OF THE INVENTION

The complete or partial detachment of ligaments, tendons and/or other soft tissues from their associated bones within the body are relatively commonplace injuries. Tissue detachment may occur as the result of an accident such as a fall, overexertion during a work-related activity, during the course of an athletic event, or in any one of many other situations and/or activities. Such injuries are generally the result of excess stress being placed on the tissues.

In the case of a partial detachment, commonly referred to under the general term "sprain", the injury frequently heals itself, if given sufficient time, and if care is taken not to expose the injury to undue stress during the healing process. If, however, the ligament or tendon is completely detached from its associated bone or bones, or if it is severed as the result of a traumatic injury, partial or permanent disability may result. Fortunately, a number of surgical procedures exist for re-attaching such detached tissues and/or completely replacing severely damaged tissues.

One such procedure involves the re-attachment of the detached tissue using "traditional" attachment devices such as staples, sutures and/or cancellous bone screws. Such traditional attachment devices have also been used to attach tendon or ligament grafts (often formed from autogenous tissue harvested from elsewhere in the body) to the desired bone or bones.

Another procedure is described in U.S. Pat. No. 4,950,270, issued Aug. 21, 1990 to Jerald A. Bowman et al. In this procedure, the damaged anterior cruciate ligament ("ACL") in a human knee, for example, is replaced by first forming bone tunnels through the tibia and femur at the points of normal attachment of the anterior cruciate ligament. Next, a ligament graft with a bone block on one of its ends is sized so as to fit within the bone tunnels. Suture is then attached to the bone block and thereafter passed through the tibial and femoral bone tunnels. The bone block is then drawn through the tibial tunnel and up into the femoral tunnel using the suture. As this is done, the graft ligament extends back out of the femoral tunnel, across the interior of the knee joint, and then through the tibial tunnel. The free end of the graft ligament resides outside the tibia, at the anterior side of the tibia. Next, a bone screw is inserted between the bone block and the wall of femoral bone tunnel so as to securely lock the bone block in position by a tight interference fit. Finally, the free end of the graft ligament is securely attached to the tibia.

In U.S. Pat. No. 5,147,362, issued Sep. 15, 1992 to E. Marlowe Goble, there is disclosed a procedure wherein aligned femoral and tibial tunnels are formed in a human knee. A bone block with a graft ligament attached thereto is passed through the tunnels to a blind end of the femoral tunnel where the block is fixed in place by an anchor. The ligament extends out the tibial tunnel, and the end thereof is attached to the tibial cortex by staples or the like. Alternatively, the end of the ligament may be fixed in the tibial tunnel by an anchor or by an interference screw.

Various types of ligament and/or suture anchors, and anchors for attaching other objects to bone, are also well known in the art. A number of these devices are described in detail in U.S. Pat. Nos. 4,898,156; 4,899,743; 4,968,315; 5,356,413; and 5,372,599, each of which is presently owned by Mitek Surgical Products, Inc. of Westwood, Mass., the assignee of this patent application.

One known method for anchoring bone blocks in bone tunnels is through "cross-pinning", in which a pin, screw or rod is driven into the bone transversely to the bone tunnel so as to intersect the bone block and thereby cross-pin the bone block in the bone tunnel. In order to provide for proper cross-pinning of the bone block in the bone tunnel, a drill guide is generally used. The drill guide serves to ensure that the transverse passage is positioned in the bone so that it will intersect the appropriate tunnel section and the bone block. Drill guides for use in effecting such transverse drilling are shown in U.S. Pat. Nos. 4,901,711; 4,985,032; 5,152,764; 5,350,380; and 5,431,651.

Other patents in which cross-pinning is discussed include U.S. Pat. Nos. 3,973,277; 5,004,474; 5,067,962; 5,266,075; 5,356,435; 5,376,119; 5,393,302; and 5,397,356.

In U.S. Pat. No. 5,431,651, issued Jul. 11, 1995 to E. Marlowe Goble, it is said that a cross-pin screw may be formed out of a material which may be absorbed by the body over time, thereby eliminating any need for the cross-pin screw to be removed in a subsequent surgical procedure.

However, such absorbable cross-pin screws as are presently known in the art lack sufficient strength to be passed directly into the bone and the bone block. Accordingly, to use absorbable cross-pin screws, one must first drill a hard metal drilling implement into the bone and bone block, remove the drilling implement, and then replace the drilling implement with the absorbable cross-pin screw. However, removal of the hard metal drilling implement often permits the bone block to shift in the tunnel, such that the subsequent insertion of the absorbable cross-pin screw becomes impossible.

Accordingly, there exists a need for a method and apparatus for fixing a bone block in a bone tunnel such that upon completion of the procedure, the bone block is cross-pinned in the bone tunnel by elements which are made of absorbable material.

OBJECTS OF THE INVENTION

The object of the present invention is, therefore, to provide a method for fixing a bone block in a bone tunnel such that the bone block is retained in the tunnel by cross-pins which are made of a material which is absorbable by the body.

A further object of the present invention is to provide devices by which the aforementioned method may be realized.

SUMMARY OF THE INVENTION

These and other objects of the present invention are addressed by the provision and use of a novel method and apparatus for fixing a bone block in a bone tunnel.

In one form of the invention, the novel method comprises the steps of placing the bone block in the bone tunnel, and then advancing spaced-apart first and second drill means through the bone transversely of the bone tunnel so as to intersect the bone block and extend therethrough. The method further includes the steps of removing one of the drill means and replacing the one removed drill means with a first absorbable rod, and then removing the other of the drill means and replacing the other removed drill means with a second absorbable rod, whereby the bone block will be retained in the bone tunnel with the absorbable rods. In one form of the invention, the first and second drill means may comprise metal wires.

The objects of the present invention are further addressed by the provision and use of an alternative method for fixing a bone block in a bone tunnel. The method comprises the steps of placing the bone block in the bone tunnel, and then advancing spaced-apart first and second trocar and sleeve assemblies through the bone, transversely of the bone tunnel, so as to intersect the bone block and extend therethrough, the trocar in each of the assemblies being disposed within one of the sleeves of the assemblies and substantially filling the sleeve. The method further includes the steps of removing the trocar from the first of the sleeves, advancing a first absorbable rod through the first sleeve and through the bone block, and then removing the first sleeve, so as to leave the first absorbable rod in the bone and the bone block. The method further includes the steps of removing the trocar from the second of the sleeves, advancing a second absorbable rod through the second sleeve and through the bone block, and then removing the second sleeve, so as to leave the second absorbable rod in the bone and the bone block, whereby the bone block will be retained in the bone tunnel with the absorbable rods.

The objects of the present invention are further addressed by the provision and use of another alternative method for fixing a bone block in a bone tunnel. The method comprises the steps of placing the bone block in the bone tunnel, and then advancing spaced-apart first and second trocar and sleeve assemblies through the bone transversely of the bone tunnel so as to intersect the bone block and extend therethrough, the trocar in each of the assemblies being disposed within one of the sleeves of the assemblies and substantially filling the sleeve. The method further includes the steps of removing the trocar from the sleeves, advancing absorbable rods through the sleeves and through the bone block, and then removing the sleeves from the bone block and the bone, so as to leave the absorbable rods in the bone block and the bone, whereby the bone block will be retained in the bone tunnel with the absorbable rods.

In accordance with a further feature of the present invention, there is provided a rack assembly for cross-pinning a bone block in a bone tunnel in a human femur, the rack assembly comprising an L-shaped member having a base portion and an arm portion extending transversely of the base portion, and a cannulated sleeve for movement through a tibia and into the femur and for disposition in the femoral bone tunnel, the cannulated sleeve having an enlarged head portion at a free end thereof for disposition in the bone tunnel in the femur and being connectable to the base portion of the L-shaped member at an opposite end thereof. The rack assembly further includes a trocar sleeve guide member removably connectable to the arm portion of the L-shaped member and having bores extending therethrough at an angle normal to a longitudinal axis of the cannulated sleeve's head portion, first and second trocar sleeves for movable disposition in the bores, respectively, and at least one trocar for disposition in the trocar sleeves, the trocar being interconnectable with the trocar sleeve in which the trocar is disposed such that the trocar sleeve and the trocar therein are movable axially toward the cannulated sleeve's head portion and rotatable together, such that the interconnected trocar and trocar sleeve are adapted for drilling into the femur and the bone block. The trocar is removable from the trocar sleeves, and absorbable rods are provided for sliding through the trocar sleeves and through the bone block, the trocar sleeves being removable from the bone block and the femur and from the absorbable rods, so as to leave the absorbable rods in the bone block and the femur.

In accordance with a still further feature of the present invention, there is provided another rack assembly for cross-pinning a bone block in a bone tunnel in a human femur. The rack assembly comprises an L-shaped member having a base portion and an arm portion extending transversely of the base portion, and a cannulated sleeve for movement through the femur until a free end thereof is disposed adjacent to the bone block, with an opposite end thereof being connectable to the base portion of the L-shaped member. A trocar sleeve guide member is removably connectable to the arm portion of the L-shaped member and is provided with bores extending therethrough at an angle normal to a hypothetical extension of a longitudinal axis of the cannulated sleeve. First and second trocar sleeves are provided for movable disposition in the bores, respectively. At least one trocar is provided for disposition in the trocar sleeves, the trocar being interconnnectable with the trocar sleeve in which the trocar is disposed such that the trocar sleeve and the trocar therein are movable axially toward the bone block and rotatable together, such that the interconnected trocar and trocar sleeve are adapted for drilling into the femur and the bone block. The trocar is removable from the trocar sleeves, and absorbable rods are slidable through the trocar sleeves and through the bone block, the trocar sleeves being removable from the bone block and the femur and from the absorbable rods so as to leave the absorbable rods in the bone block and the femur.

BRIEF DESCRIPTION OF THE DRAWINGS

The above and other objects and features of the present invention will be more fully discussed in, or rendered obvious by, the following detailed description of the preferred embodiments of the invention, which is to be considered together with the accompanying drawings wherein like members refer to like parts, and further wherein:

FIG. 10 is a side elevational view of one form of rack assembly for cross-pinning a bone block in a bone tunnel, illustrative of an embodiment of the invention;

FIG. 11 is a bottom view of the rack assembly of FIG. 10;

FIG. 12 is a bottom view of a trocar sleeve guide member portion of the rack assembly of FIGS. 10 and 11;

FIG. 13 is a side elevational view of the trocar sleeve guide member;

FIG. 14 is a front elevational view of the trocar sleeve guide member;

FIG. 15 is an interrupted side elevational view of a trocar portion of the rack assembly of FIG. 10;

FIG. 16 is an interrupted side elevational view, broken away and partly in section, of a trocar sleeve portion of the rack assembly of FIG. 10;

FIG. 17 is an end view of the trocar sleeve portion of FIG. 16;

FIG. 31 is a bottom view of a trocar sleeve guide member portion of the rack assembly of FIG. 29;

FIG. 32 is a side elevational view of the trocar sleeve guide member;

FIG. 33 is a front elevational view of the trocar sleeve guide member;

DETAILED DESCRIPTION OF THE PREFERRED EMBODIMENTS

Figure 1:
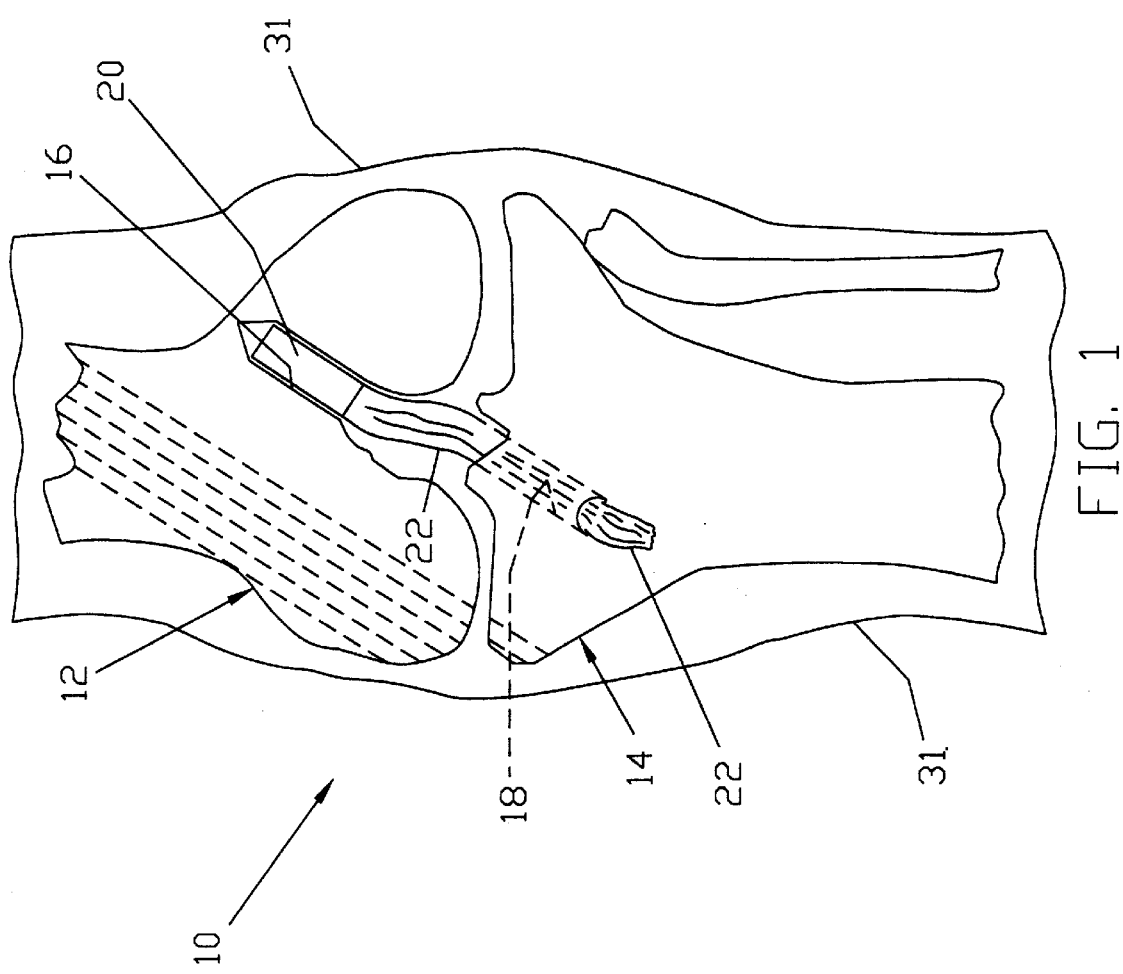
FIG. 1 is a diagrammatical sectional view of a human knee joint, with appropriate bone tunnels formed therein and with a ligament bone block disposed in one of the tunnels.

Referring first to FIG. 1, it will be seen that a human knee joint 10, including a femur 12 and tibia 14, has been provided with an appropriate femoral bone tunnel 16 and an appropriate tibial bone tunnel 18. Such tunnels may be provided in ways well known in the art. A bone block 20, having ligament material 22 attached thereto, has been positioned in femoral tunnel 16. Such bone block positioning may also be achieved in ways well known in the art.

Figure 2:
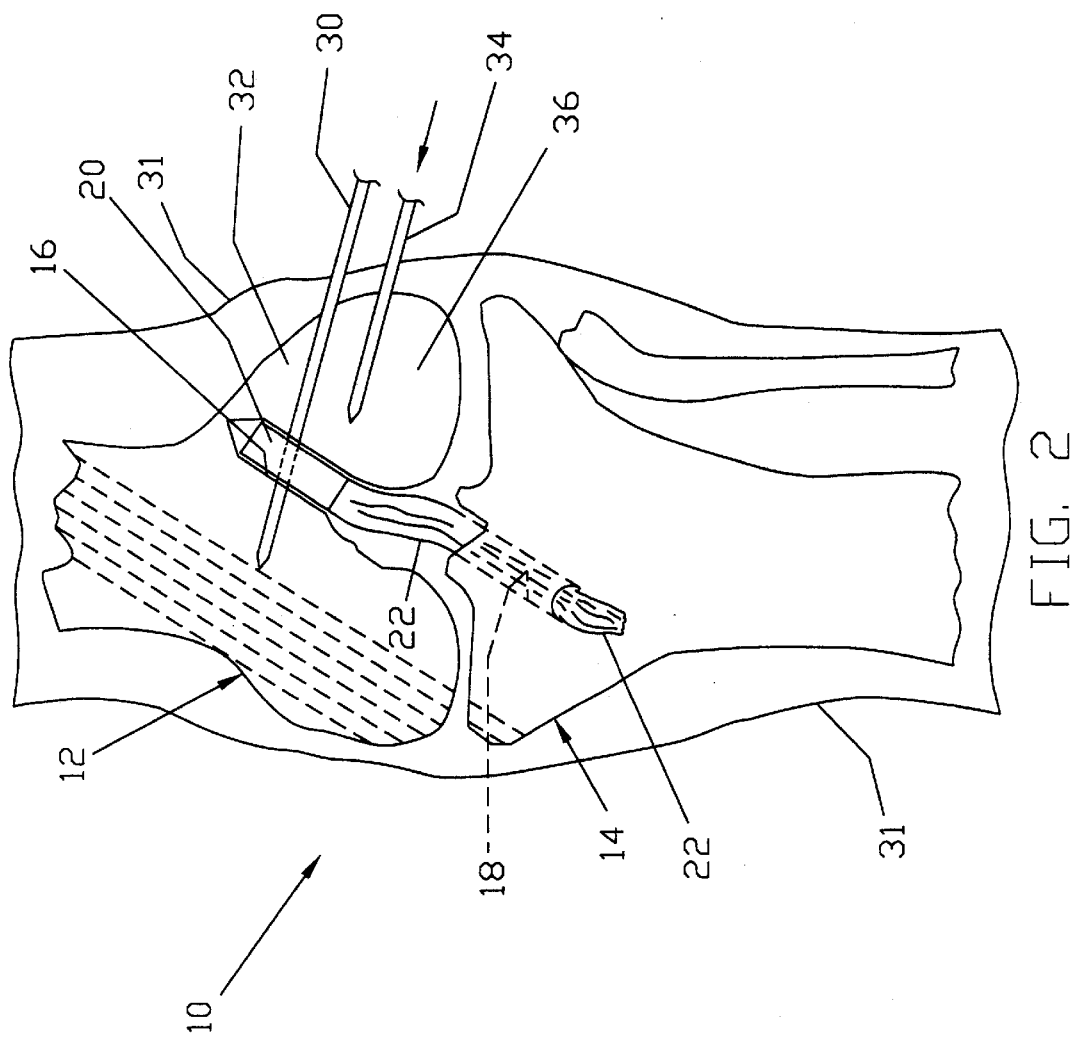
FIG. 2 is similar to FIG. 1, but illustrative of a metal wire insertion phase of the inventive method.
Figure 3:
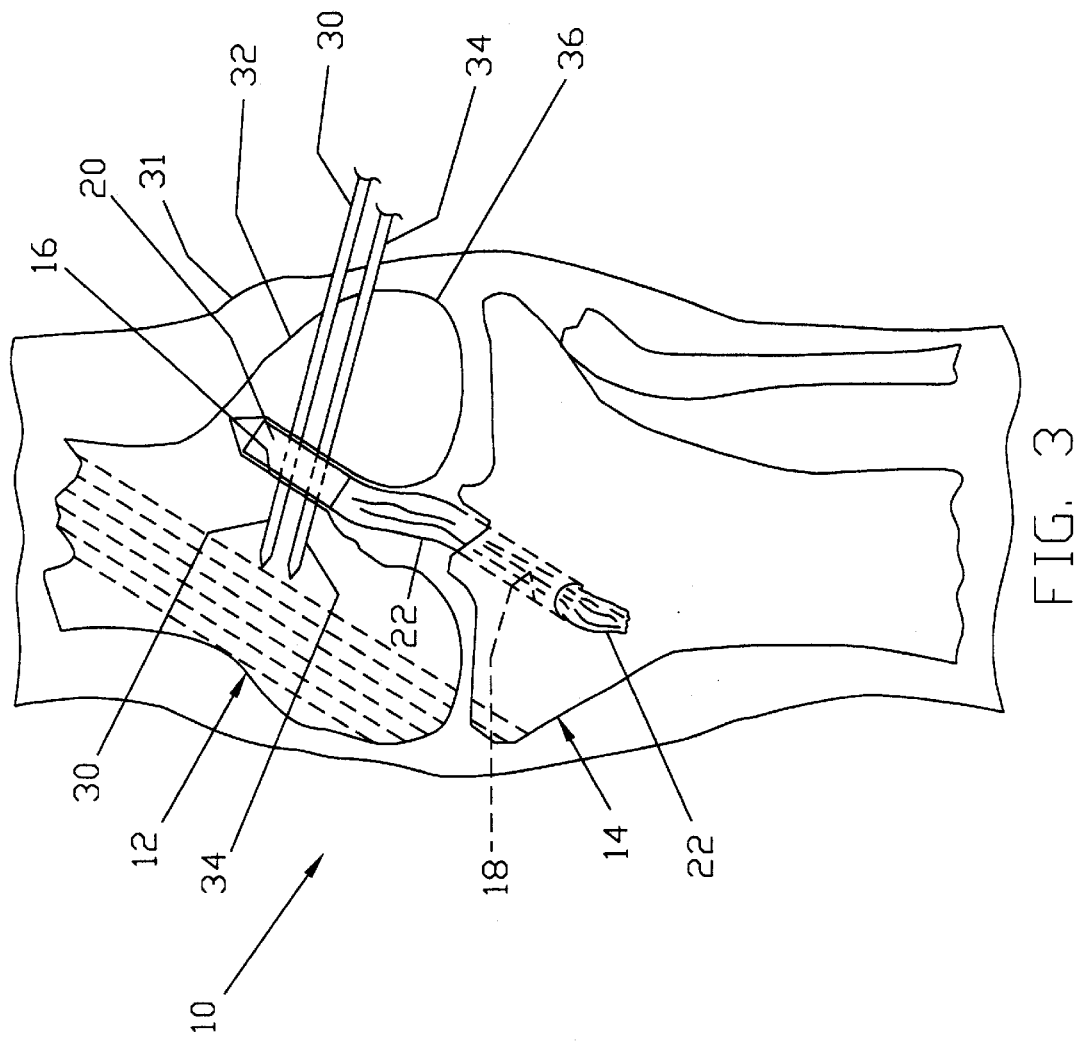
FIG. 3 is similar to FIG. 2 but illustrative of completion of the metal wire insertion phase.

Looking next at FIG. 2, in accordance with the present invention, a first metal wire 30, which may be of the type commonly referred to as a guidewire or a "K-wire", is advanced through skin 31 and a first portion 32 of femur 12. First wire 30 is advanced transversely of femoral tunnel 16 so as to intersect and extend through bone block 20, as shown in FIG. 2. Thereafter, or simultaneously therewith, a second metal wire 34 is advanced through a second portion 36 of femur 12. Second wire 34 is also advanced transversely of femoral tunnel 16 so as to also intersect and extend through bone block 20 (FIG. 3). At this point, bone block 20 is securely held in femoral tunnel 16 by the two spaced-apart metal wires 30, 34.

Figure 4:
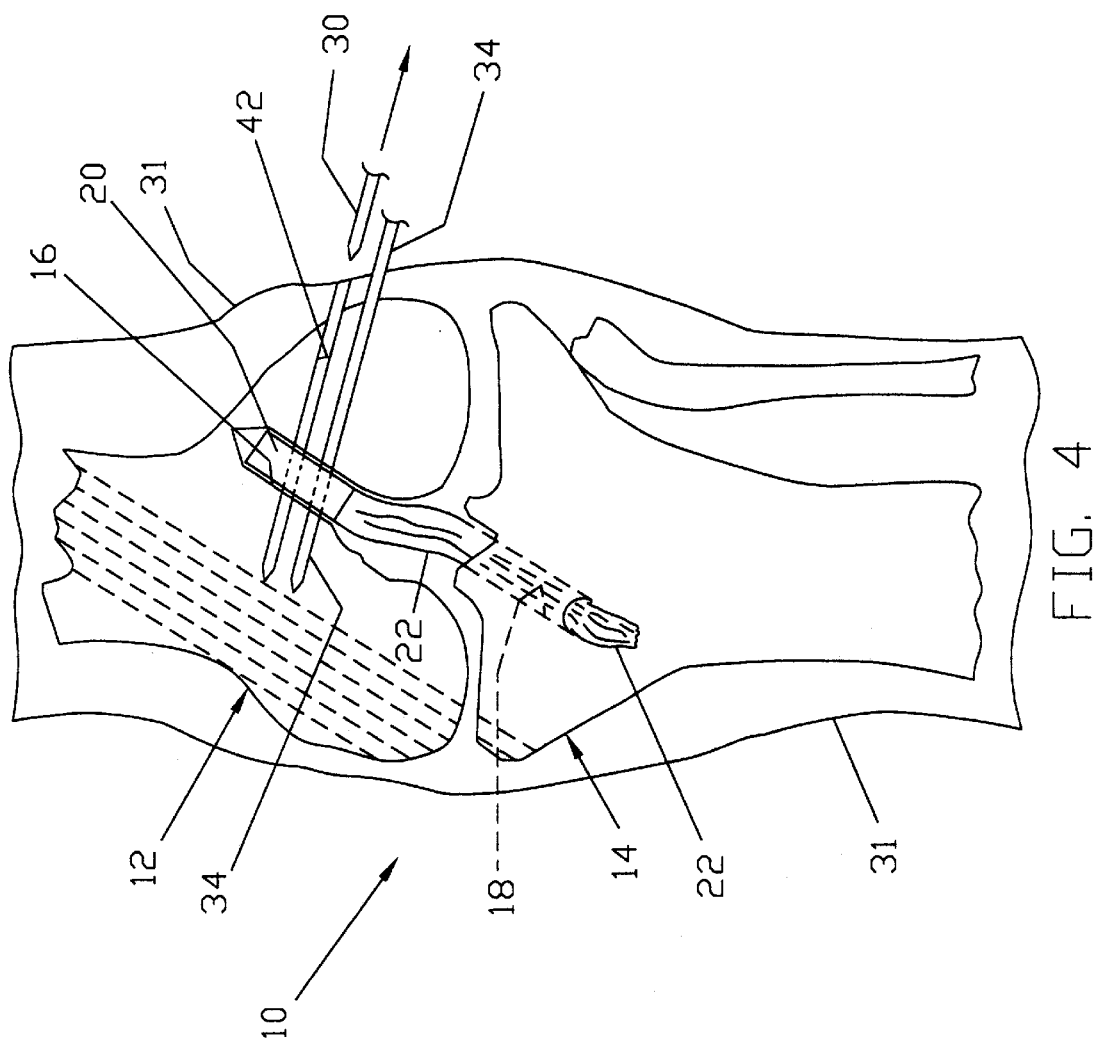
FIG. 4 is similar to FIG. 3, but illustrative of a first metal wire withdrawal phase.
Figure 5:
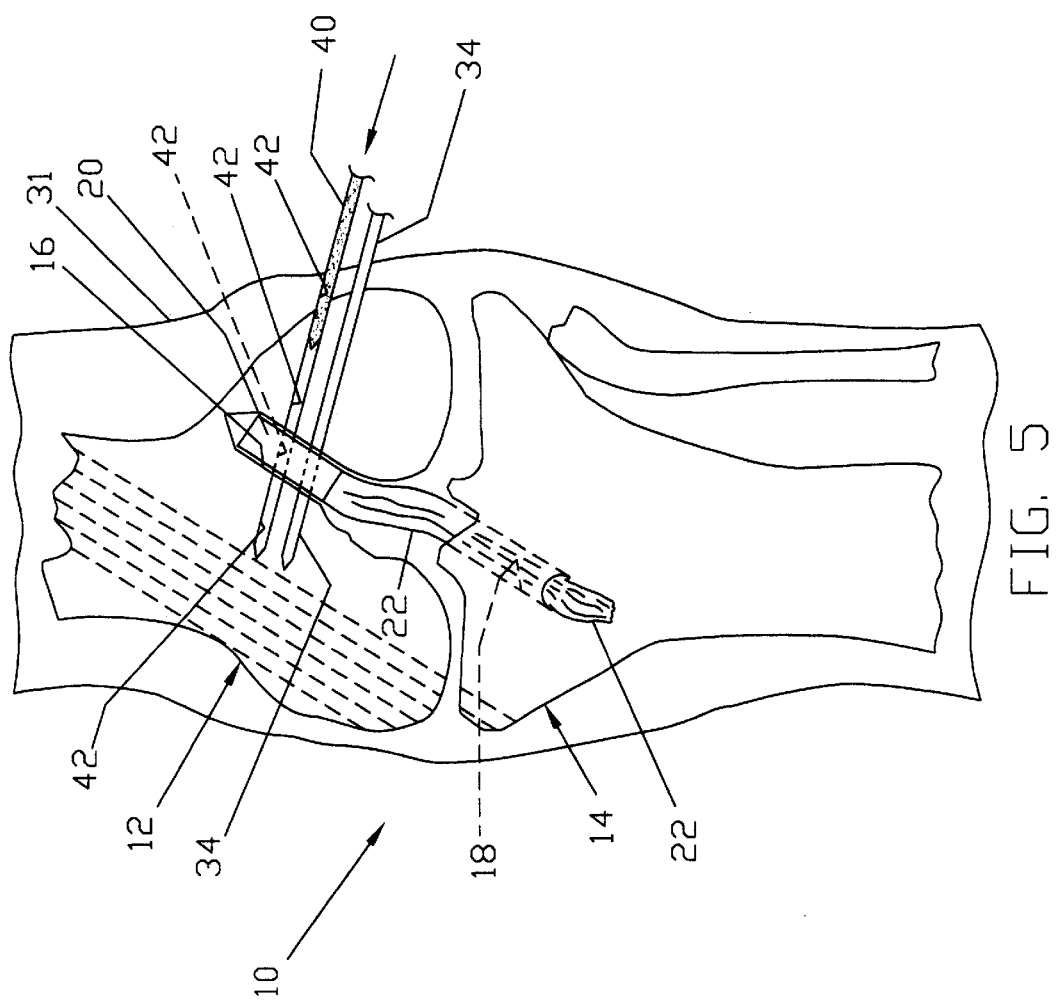
FIG. 5 is similar to FIG. 4, but illustrative of a first absorbable rod insertion phase.
Figure 6:
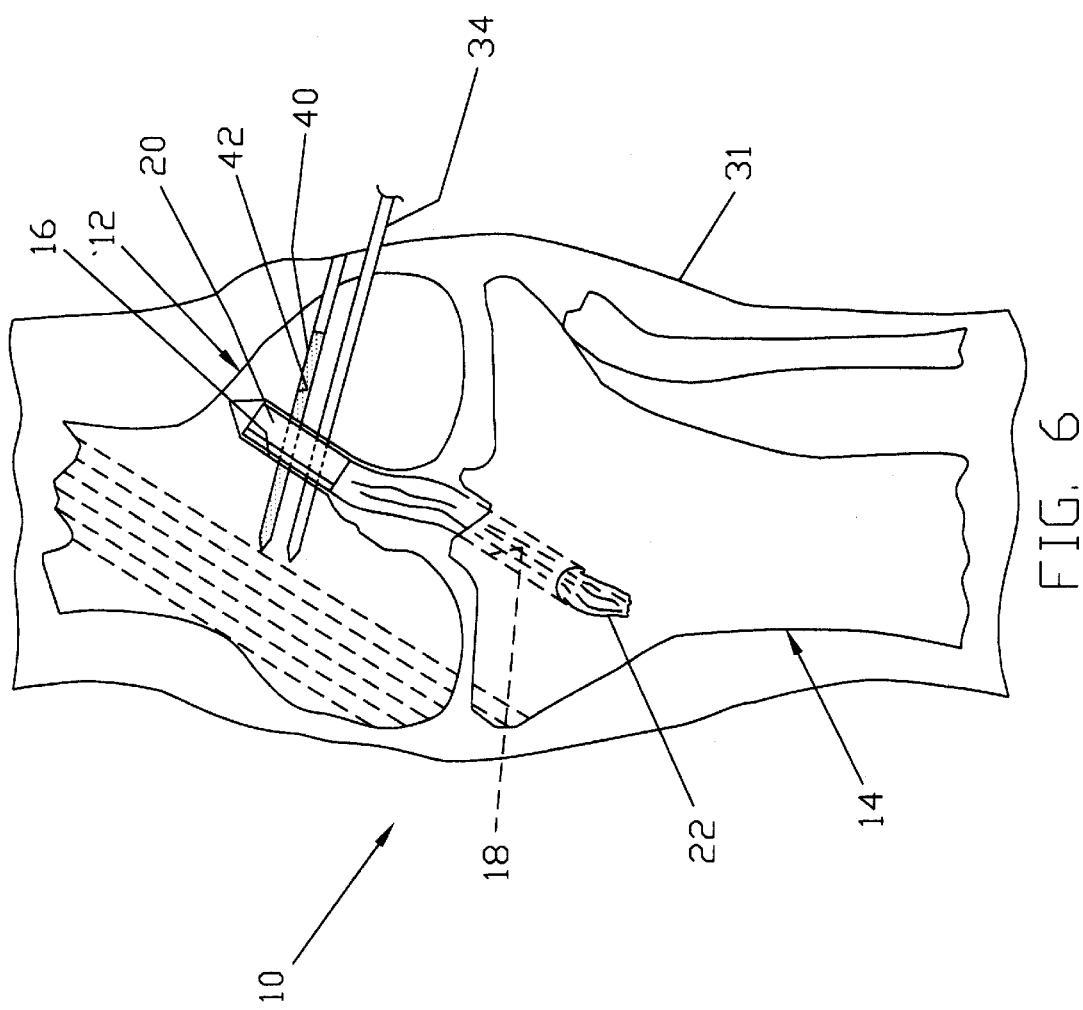
FIG. 6 is similar to FIG. 5, but illustrative of the first absorbable rod having been fully inserted.

Referring next to FIG. 4, it will be seen that one of the two wires 30, 34 is then removed, while the other of the two wires 30, 34 is left in place in femur 12 and bone block 20. By way of example but not limitation, wire 30 may be removed while wire 34 is left in place. A first absorbable rod 40 (FIG. 5) is then advanced through the bore 42 left by the removal of first wire 30, such that first absorbable rod 40 extends through femur 12 and bone block 20 (FIG. 6). At this point, bone block 20 is securely held in femoral tunnel 16 by both metal wire 34 and first absorbable rod 40.

Figure 7:
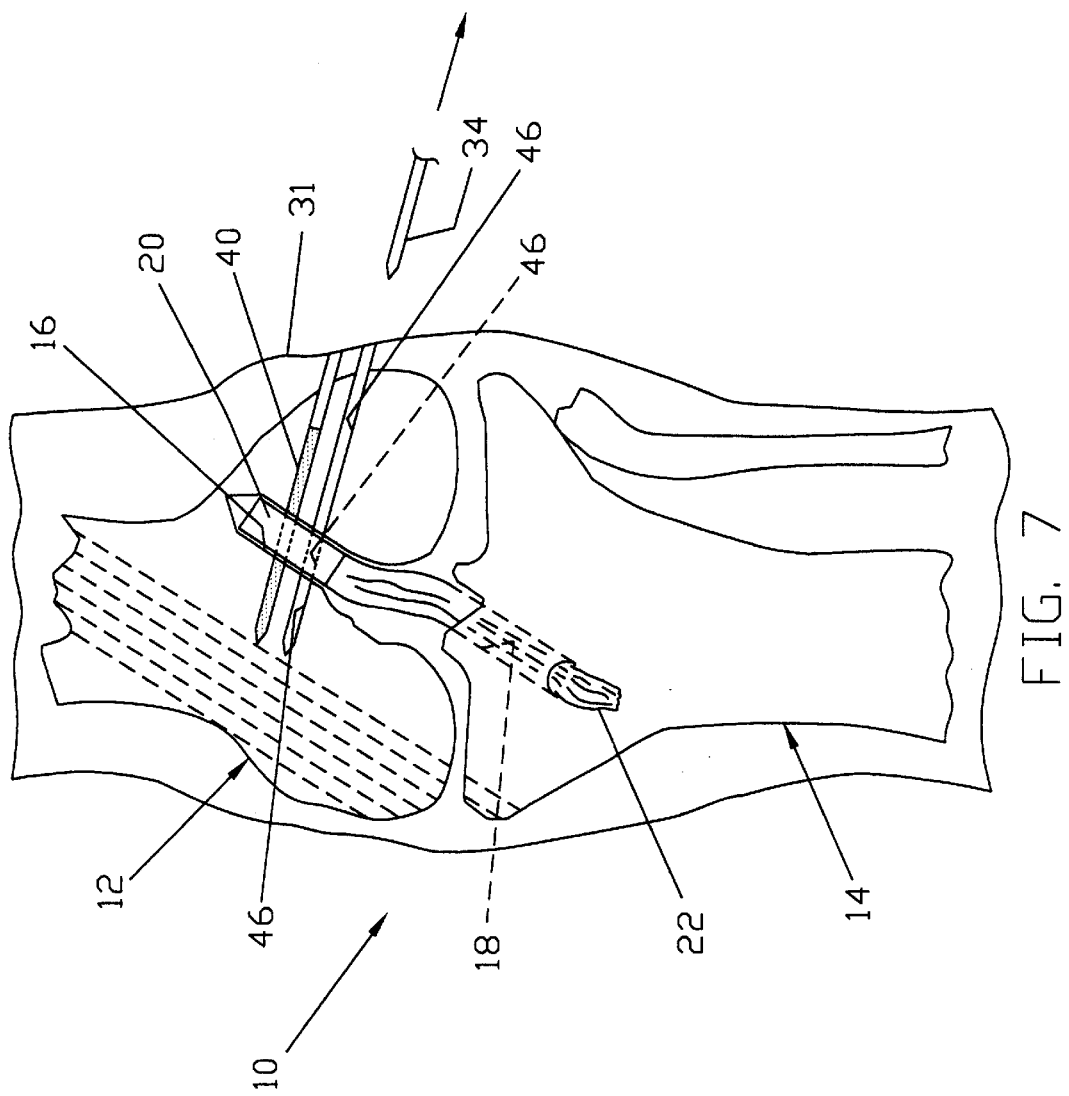
FIG. 7 is similar to FIG. 6, but illustrative of a second metal wire withdrawal phase.
Figure 8:
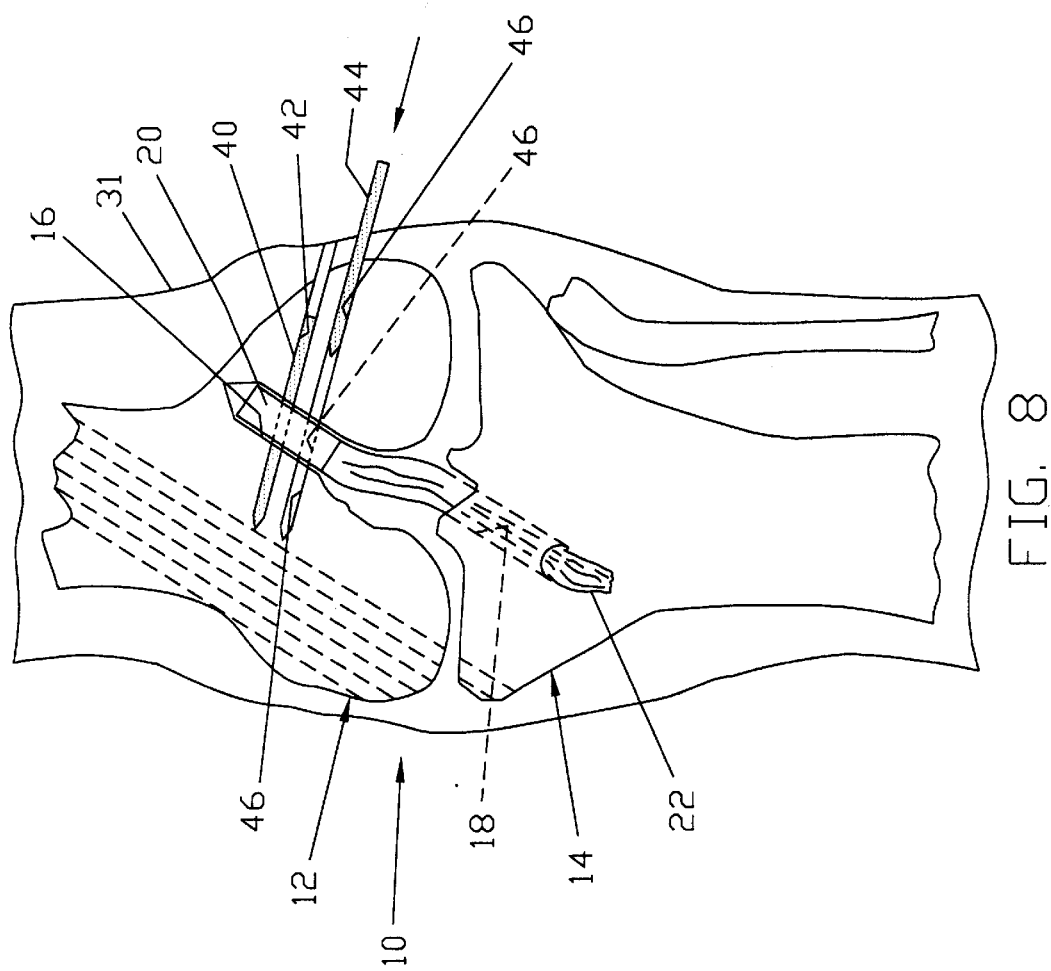
FIG. 8 is similar to FIG. 7, but illustrative of a second absorbable rod insertion phase.
Figure 9:
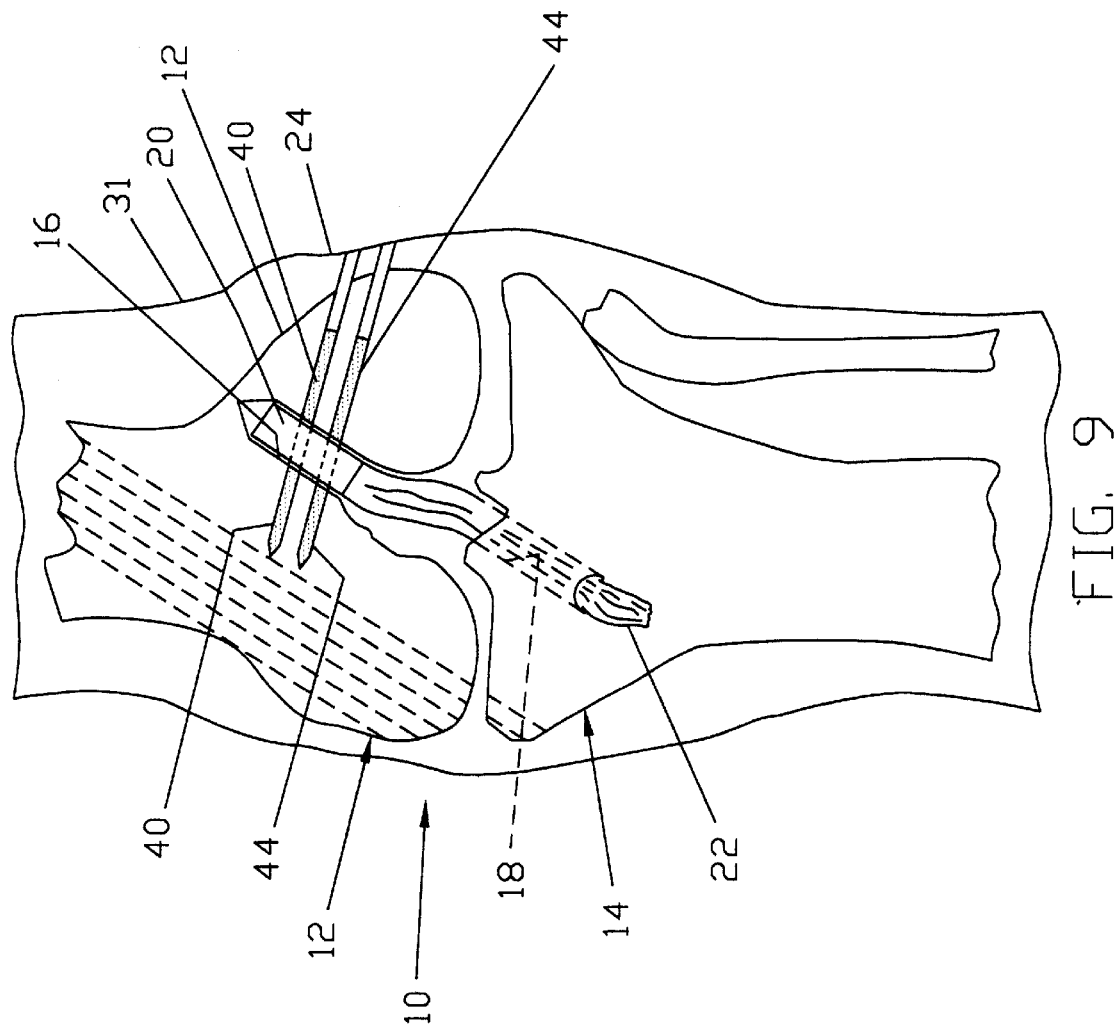
FIG. 9 is similar to FIG. 8, but illustrative of the completion of the absorbable rod insertion phase of the inventive method.

Thereafter, the other of the two metal wires 30, 34 is withdrawn (e.g., in FIG. 7, metal wire 34 is removed), and a second absorbable rod 44 (FIG. 8) is advanced through the bore 46 left by the removal of metal wire 34, such that second absorbable rod 44 also extends through femur 12 and bone block 20 (FIG. 9).

It will be appreciated that, upon completion of the insertion of second absorbable rod 44 (FIG. 9), bone block 20 is retained in femoral tunnel 16 solely by the absorbable rods 40, 44.

The absorbable rods 40, 44 may be made out of a material such as polylactic acid (PLA), polyglycolic acid (PGA), polydiaxanone (PDS), or out of some other such material which is formable into a relatively rigid and hard configuration, but which is absorbable by the body of the patient over time. If desired, the distal ends of absorbable rods 40, 44 can be pointed or rounded so as to facilitate their deployment into the body.

There is thus provided a method by which a bone block is fixed within a bone tunnel, such that the bone block is anchored in the tunnel by cross-pins which are made out of a material which is absorbable by the body over time.

It will be understood that while the above method has been described and illustrated with respect to first and second wires replaced serially by first and second absorbable rods, the method may be exercised with any reasonable number of wires, exceeding one. In the latter instance, the method includes the steps of placing the bone block in the bone tunnel, and then advancing a plurality of metal wires through the bone, transversely of the tunnel, so as to intercept the bone block and extend therethrough. At least one of the wires is then removed while leaving at least one of the wires in place, and that at least one removed wire is then replaced by at least one absorbable rod. At least one further of the wires is then removed and that at least one removed wire is then replaced by at least one further absorbable rod. The last-mentioned step is then repeated until a selected number of the metal wires is each replaced with an absorbable rod, whereby to retain the bone block in the bone tunnel with absorbable rods.

It will also be understood that while FIGS. 1–9 show metal wires 30, 34 and absorbable rods 40, 44 passing completely through bone block 20 during the cross-pinning procedure, it is also possible for metal wires 30, 34 and absorbable rods 40, 44 to pass only part way across bone block 20, if the same should be desired.

Furthermore, it will also be understood that while the above method has been described and illustrated with respect to metal wires 30, 34 being used to drill through femur 12 and bone block 20, other drilling implements (e.g., a twist drill or a spade drill) might also be used.

As noted above, various drill guides have been developed for forming transverse passages through the femur and bone block so as to cross-pin the bone block within the femoral tunnel. If desired, the inventive method of the present invention may be practiced using such known drill guides. Alternatively, the present invention may also be practiced using a novel rack assembly formed in accordance with the present invention.

More particularly, and looking now at FIGS. 10–17, a novel rack assembly 50 is disclosed for practicing the present invention. Rack assembly 50 comprises an L-shaped member 52 having a base portion 54 and an arm portion 56. The arm portion 56 extends transversely, and preferably is normal to, base portion 54.

Rack assembly 50 also includes a cannulated sleeve 58 which, at a first end 60 thereof, is provided with an enlarged head portion 62, and which, at a second end 64 thereof, is releasably connectable to base portion 54 of L-shaped member 52. Sleeve 58 may be retained in a bore 65 (FIG. 11) formed in base portion 54 by a set screw 66.

A trocar sleeve guide member 70 is removably connectable to arm portion 56 of L-shaped member 52. Trocar sleeve guide member 70 is provided with bores 72 extending therethrough. Bores 72 extend substantially normal to a longitudinal axis 68 (FIG. 10) of the enlarged head portion 62 of cannulated sleeve 58. A set screw 71 (FIG. 11) may be used to releasably retain trocar sleeve guide member 70 in position on arm portion 56. Alternatively, or in addition, arm portion 56 may be provided with stop means (not shown) for limiting the movement of the trocar sleeve guide member 70 along arm portion 56. Trocar sleeve guide member 70 is preferably formed in two halves releasably held together by a set screw 73 (FIG. 11), whereby trocar sleeve guide member 70 can be slidably mounted on, or detached from, trocar sleeves 74, 76 passing through bores 72, as will hereinafter be discussed.

First and second trocar sleeves 74, 76 are slidably received by bores 72, such that sleeves 74, 76 are axially and rotatably movable in bores 72. Referring to FIGS. 16 and 17, it will be seen that trocar sleeve 74 is provided with a collar portion 78 having a slot 80 formed therein. Sleeve 76 is substantially identical to sleeve 74.

Rack assembly 50 also includes one or more trocars 82 (FIGS. 10 and 15) for disposition in the sleeves 74, 76. Each trocar 82 is provided with a sharp end 84 (FIG. 15) for penetration of bone. A transversely-extending pin 86 is provided near (but spaced from) the opposite end of the trocar 82. Pin 86 is fixed in place and is receivable by the slots 80 of trocar sleeves 74, 76 such that axial (in a distal direction) and rotational movement of trocar 82 causes similar movement of sleeves 74, 76.

The first and second absorbable rods 40, 44 are slidable through sleeves 74, 76, as will be further described hereinbelow.

FIGS. 18–28 illustrate how rack assembly 50 may be used to practice the present invention.

Figure 18:
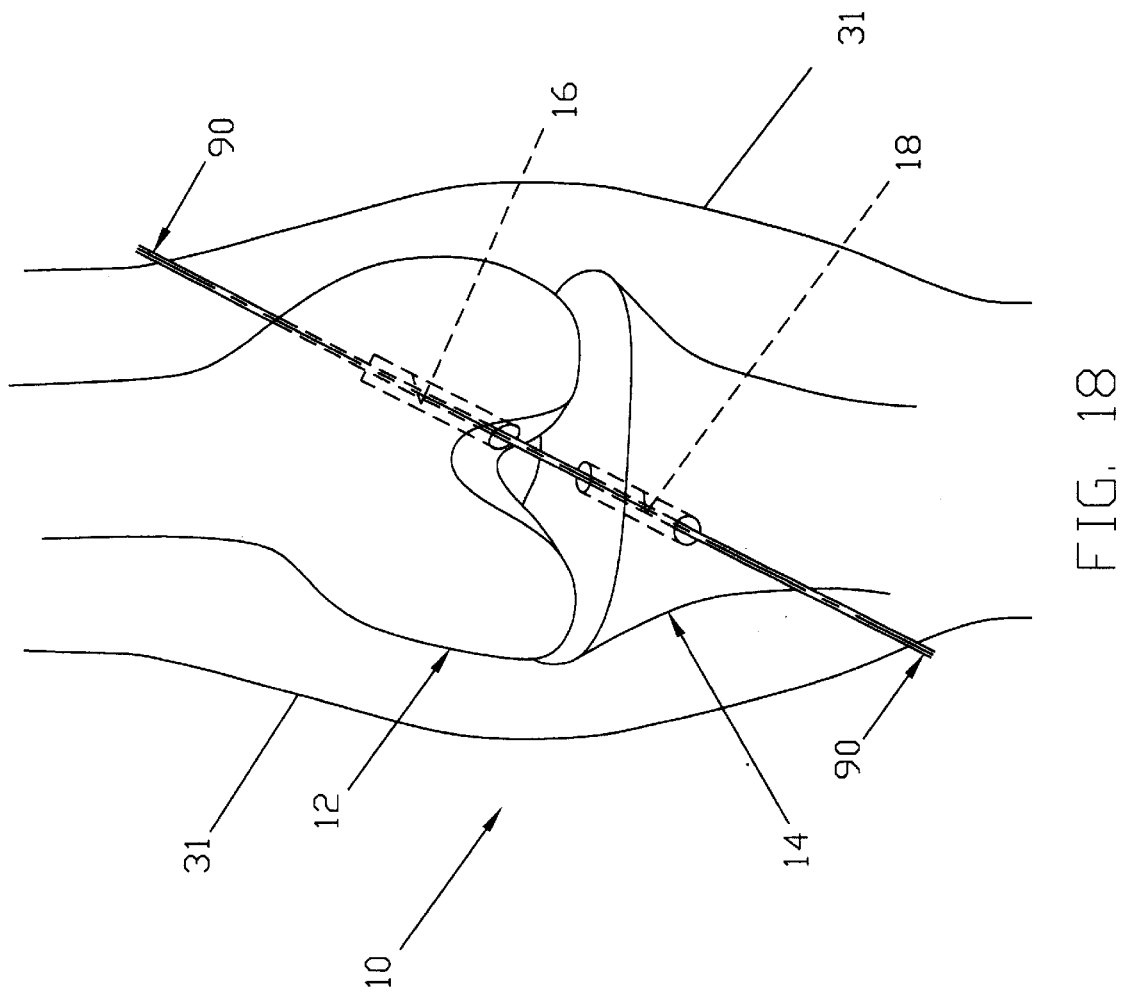
FIG. 18 is a diagrammatical view of a human knee joint and illustrative of a step in a method in which the rack assembly of FIG. 10 is used.

Referring now to FIG. 18, there is shown a human knee joint 10 including femur 12 and tibia 14. An appropriate femoral tunnel 16 and an appropriate tibial tunnel 18 have been provided, as by means and methods well known in the art. A guidewire 90 extends through the bone tunnels 16, 18 as shown.

Figure 19:
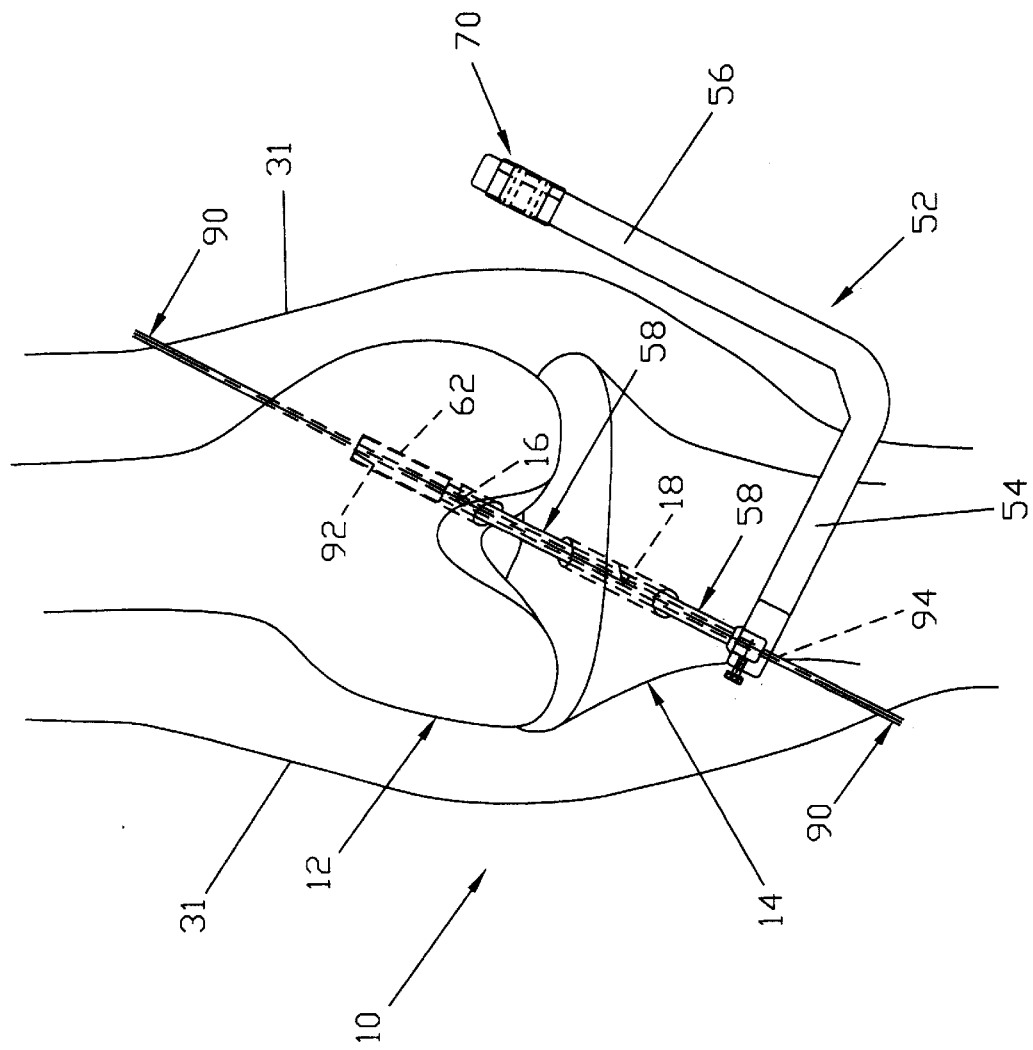
FIGS. 19–28 are diagrammatical views illustrating a series of steps in the use of the rack assembly of FIG. 10.

In accordance with the present invention, the rack assembly's cannulated sleeve 58 is fed over guidewire 90, through tibial tunnel 18 and into femoral tunnel 16, until the cannulated sleeve's head portion 62 engages an annular shoulder 92 in femoral tunnel 16 (FIG. 19). As this occurs, guidewire 90 extends through a bore 94 (FIGS. 10 and 19) formed in base portion 54 of L-shaped member 52. The cannulated sleeve's head portion 62 is preferably sized so as to form a snug fit in femoral tunnel 16. Cannulated sleeve 58 may be positioned in the bone tunnels 16, 18 and then connected to L-shaped member 52 or, more preferably, cannulated sleeve 58 may be first connected to L-shaped member 52 and then positioned in femur 12 and tibia 14. Trocar sleeve guide member 70, if not already positioned on arm portion 56, is then fixed to arm portion 56, as by set screw 71 (FIG. 11).

Figure 20:
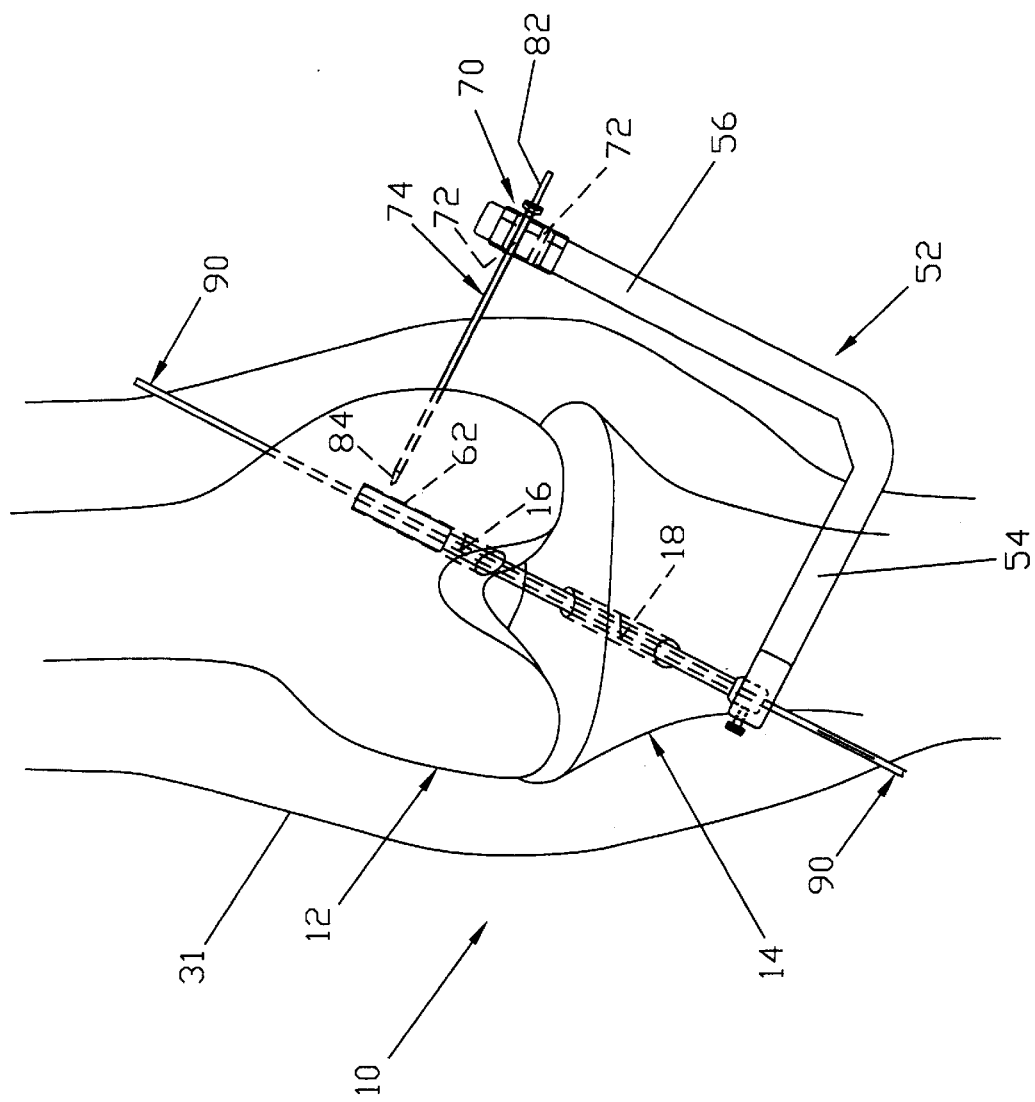

First trocar sleeve 74 is then inserted in a bore 72 of guide member 70 (FIG. 20), and trocar 82 is extended through sleeve 74 until pin 86 (FIG. 15) of trocar 82 is nested in slot 80 (FIGS. 16 and 17) of sleeve 74, with the trocar's sharp end 84 extending beyond the distal end of sleeve 74 (FIG. 20). Alternatively, trocar 82 may be mounted in first trocar sleeve 74 before first trocar sleeve 74 is mounted in a bore 72. The combination of trocar sleeve 74 and trocar 82 is then drilled, as a unit, into femur 12 toward, but short of, the enlarged head portion 62 of cannulated sleeve 58 (FIG. 20).

Figure 21:
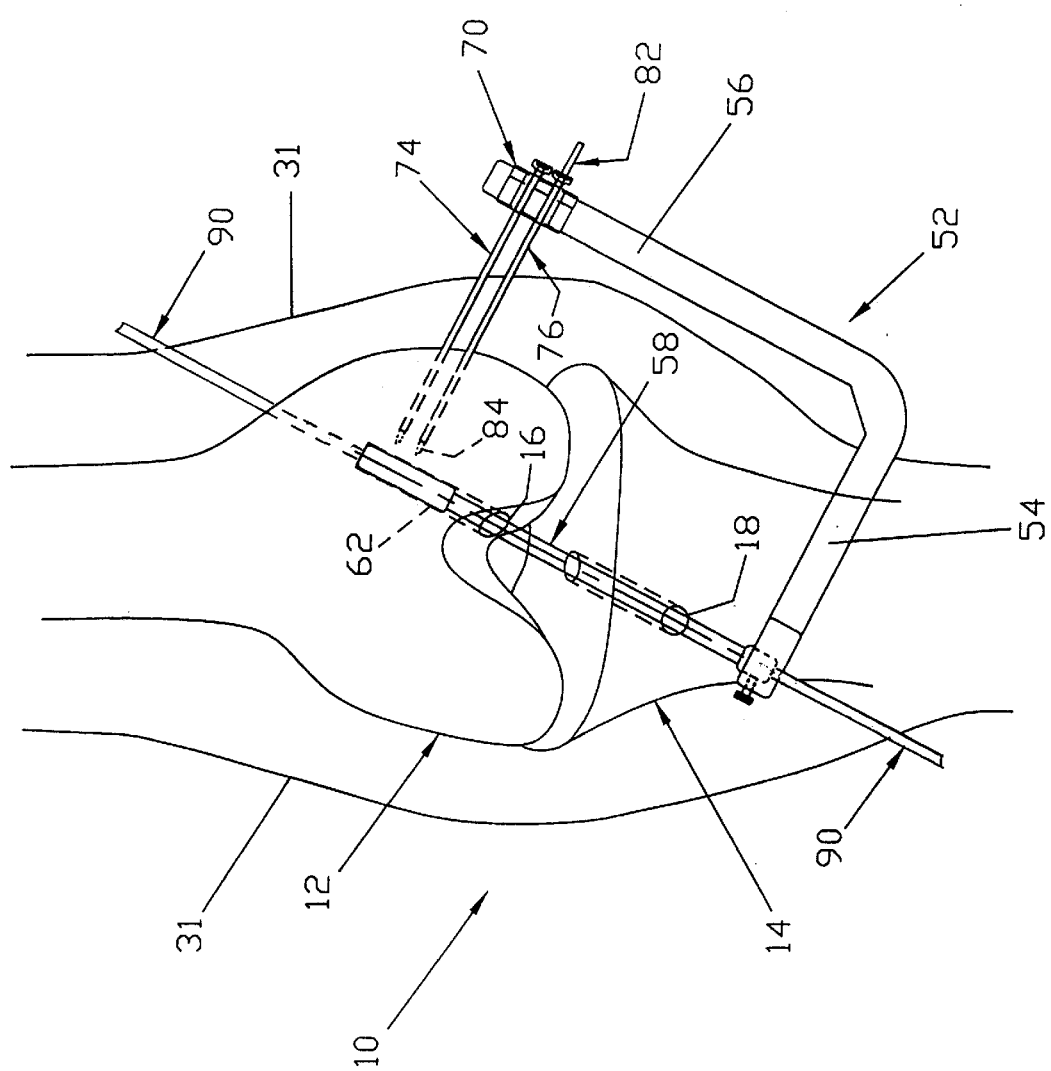
Figure 22:
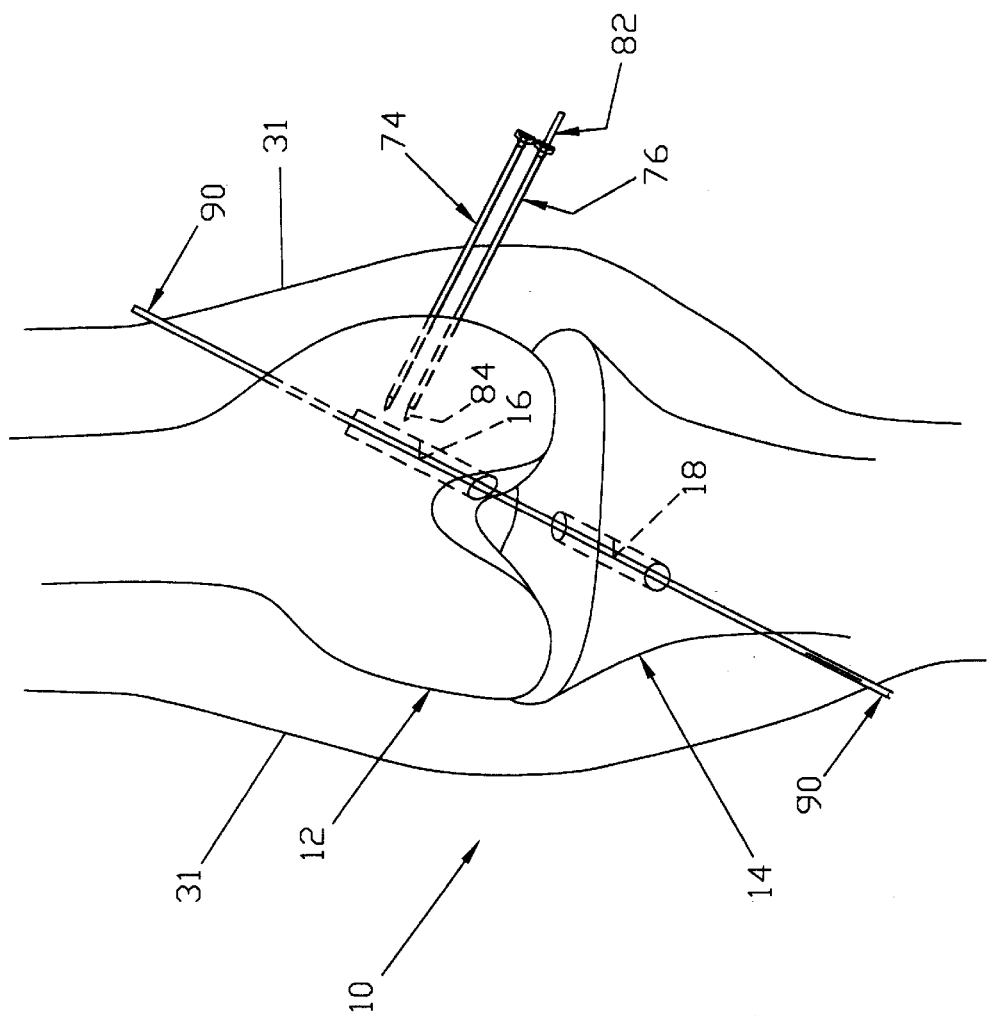

Trocar 82 may then be withdrawn from first trocar sleeve 74 and placed in second trocar sleeve 76 (FIG. 21). Alternatively, a second trocar 82 may be provided for second trocar sleeve 76. In either case, the combination of trocar sleeve 76 and trocar 82 is then drilled, as a unit, into femur 12 toward, but short of, head portion 62 of cannulated sleeve 58. The rack's L-shaped member 52 may then be removed from the surgical site. This may be accomplished by first loosening set screw 73 (FIG. 11) so as to separate trocar sleeve guide member 70 into its two halves, whereby trocar sleeves 74, 76 will be freed from guide member 70, and then sliding cannulated sleeve 58 downward along guidewire 90 until the cannulated sleeve emerges from bone tunnels 16, 18. This procedure will leave trocar sleeves 74, 76 lodged in femur 12 (FIG. 22).

Figure 23:
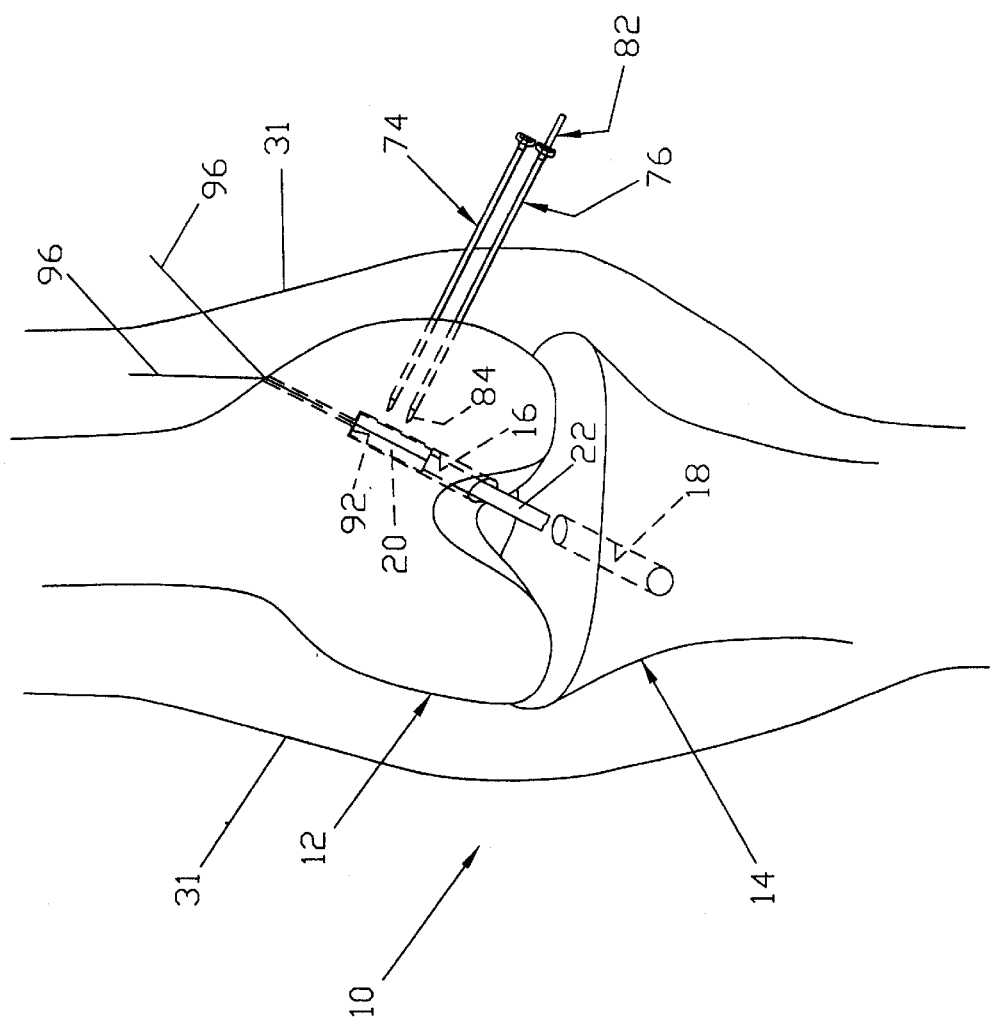

Guidewire 90 is then used to pull a suture 96, which is attached to bone block 20, up through tibial tunnel 18 and into femoral tunnel 16, until bone block 20 engages the annular shoulder 92 in femoral tunnel 16 (FIG. 23). Guidewire 90 may be provided with an eyelet (not shown) adjacent to its proximal end so as to facilitate this procedure. Bone block 20 can then be held is this position by maintaining tension on the portion of suture 96 emerging from the top of femur 12.

Figure 24:
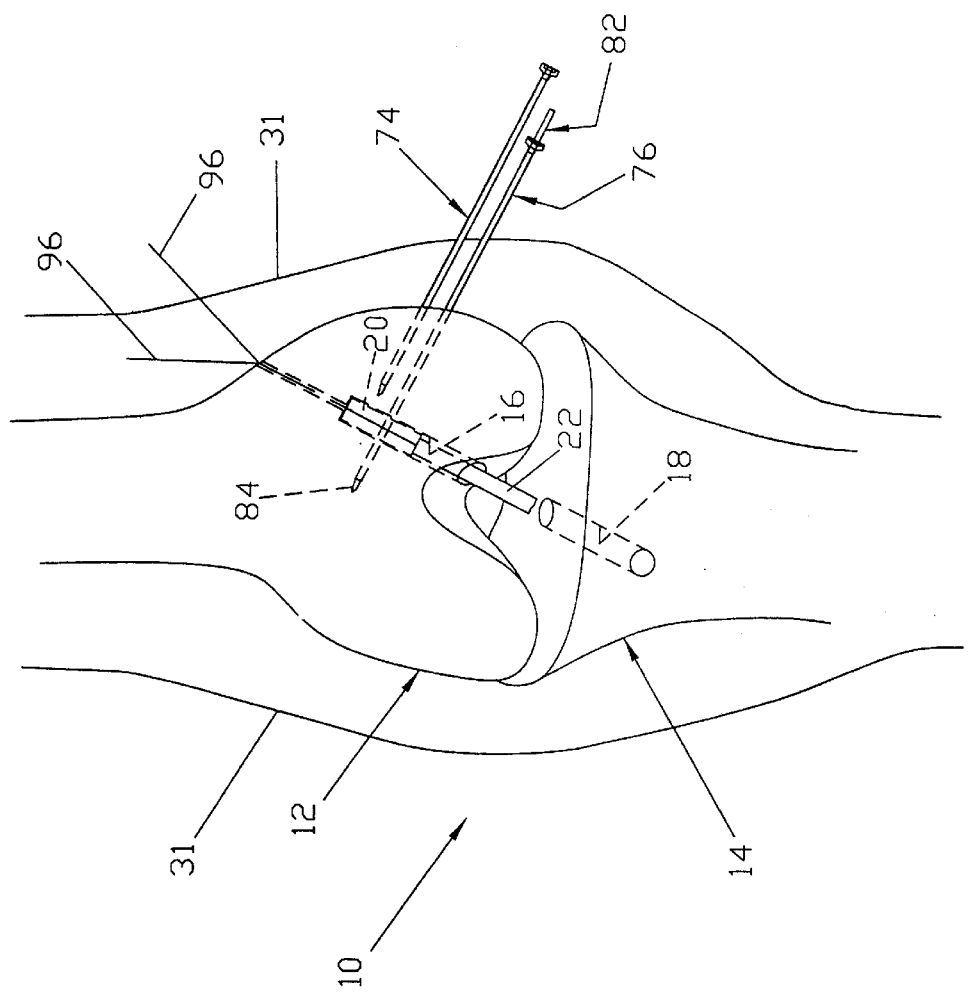
Figure 25:
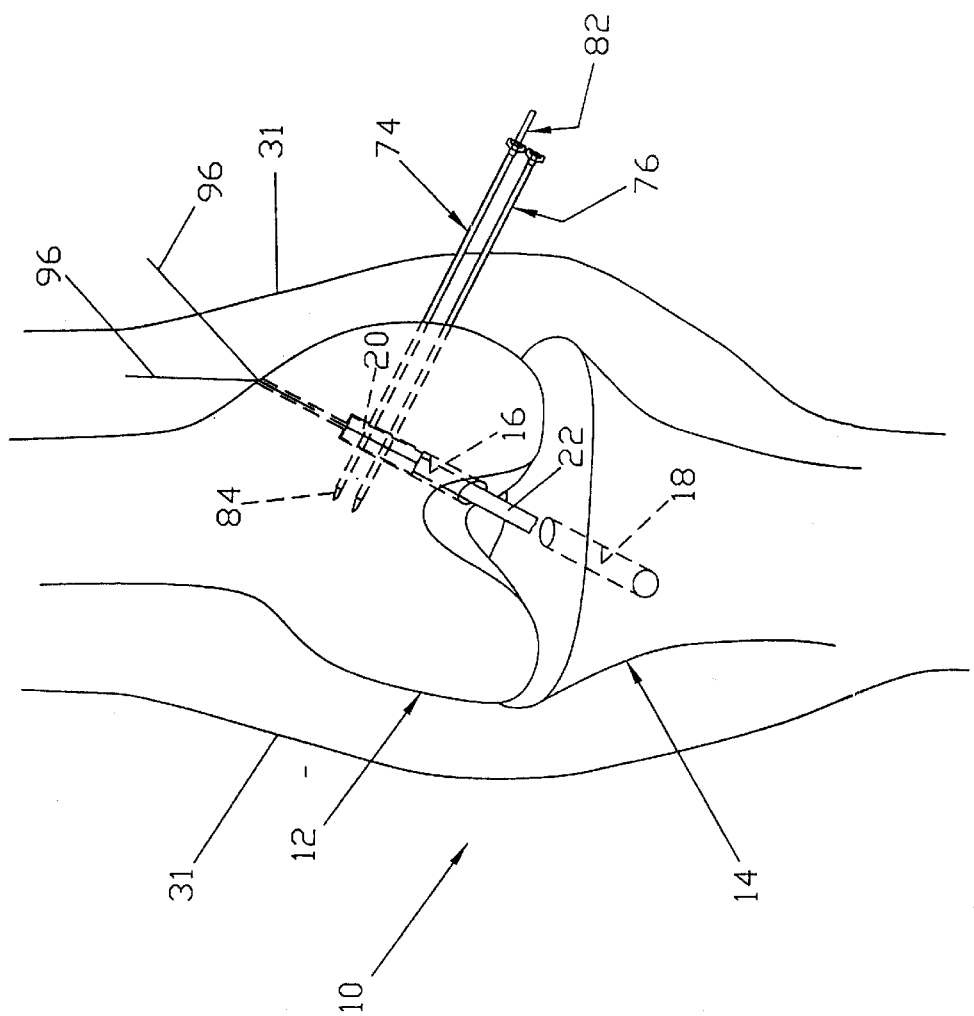
Figure 26:
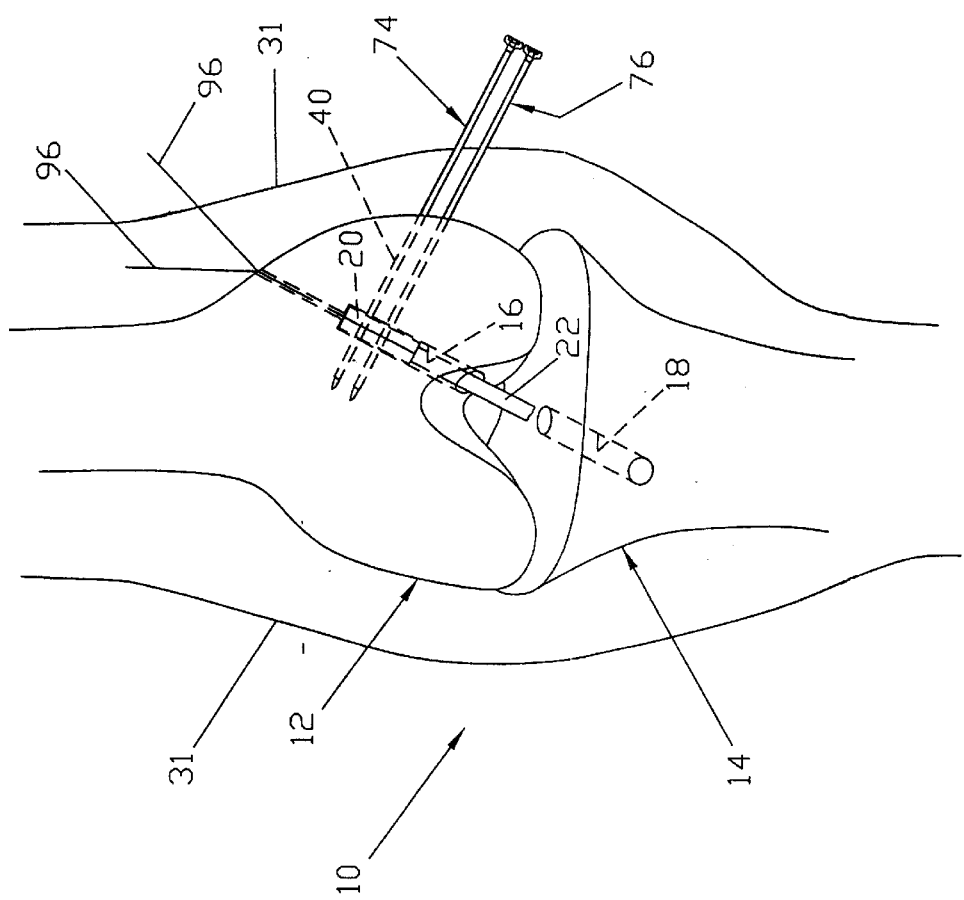
Figure 27:
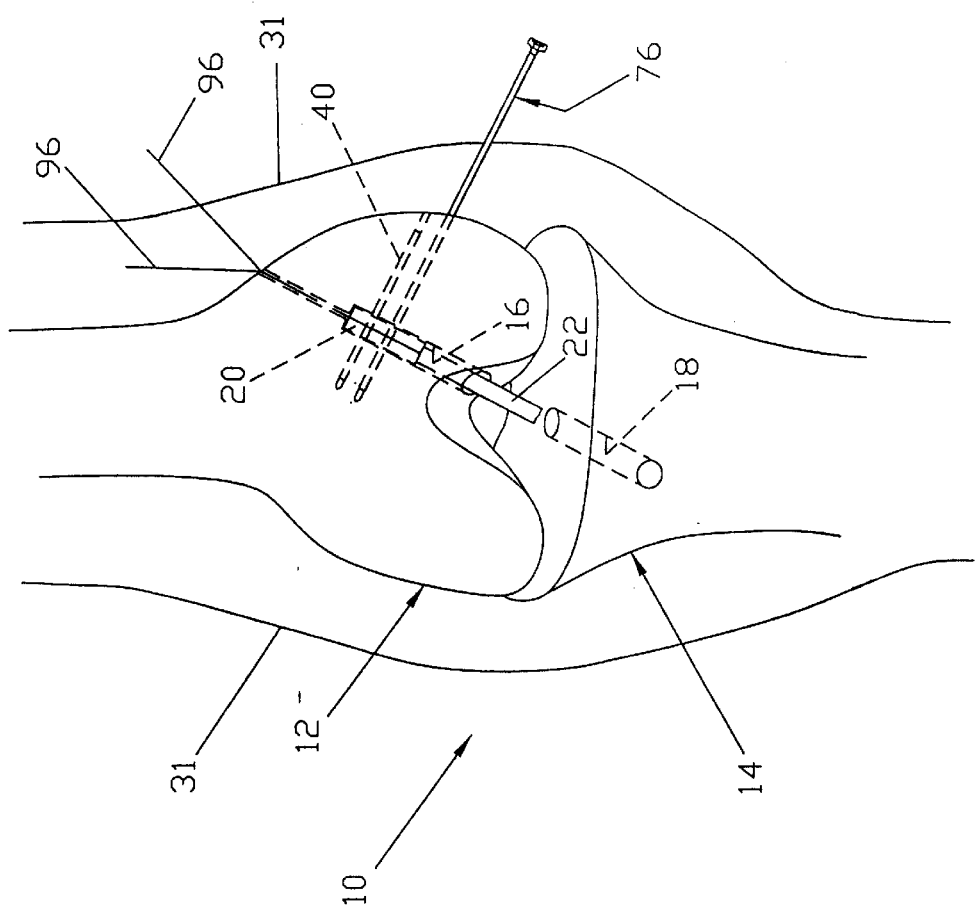

Trocar sleeve 76 and trocar 82 are then drilled through bone block 20, as shown in FIG. 24. Trocar 82 may then be removed from sleeve 76, placed in sleeve 74, and sleeve 74 and trocar 82 drilled through bone block 20, as shown in FIG. 25. The trocar 82 (or trocars 82 if more than one trocar is used) may then be withdrawn from the sleeve 74 (or sleeves 74, 76). The first absorbable rod 40 is then inserted, by sliding rod 40 through trocar sleeve 74 into a position extending through bone block 20 (FIG. 26). Sleeve 74 may then be withdrawn from bone block 20 and femur 12, leaving first absorbable rod 40 in place in femur 12 and extending through bone block 20, as shown in FIG. 27.

Figure 28:
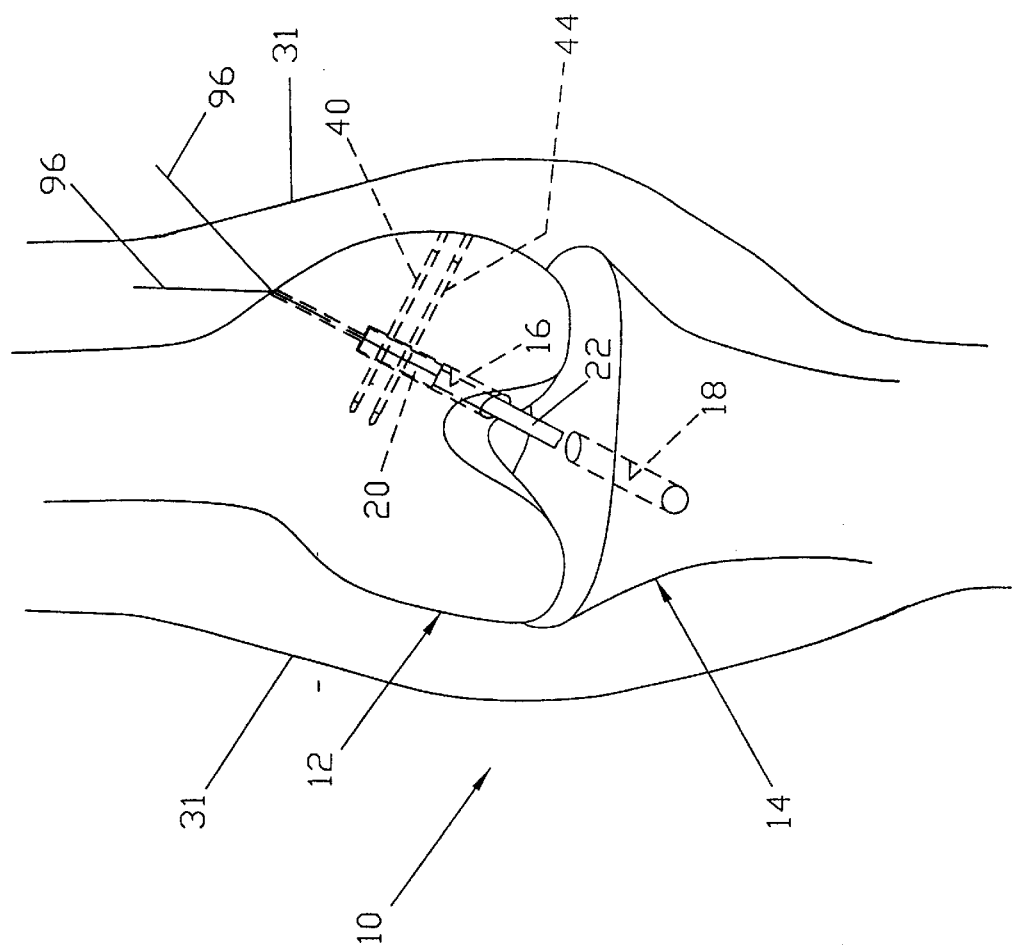
Figure 29:
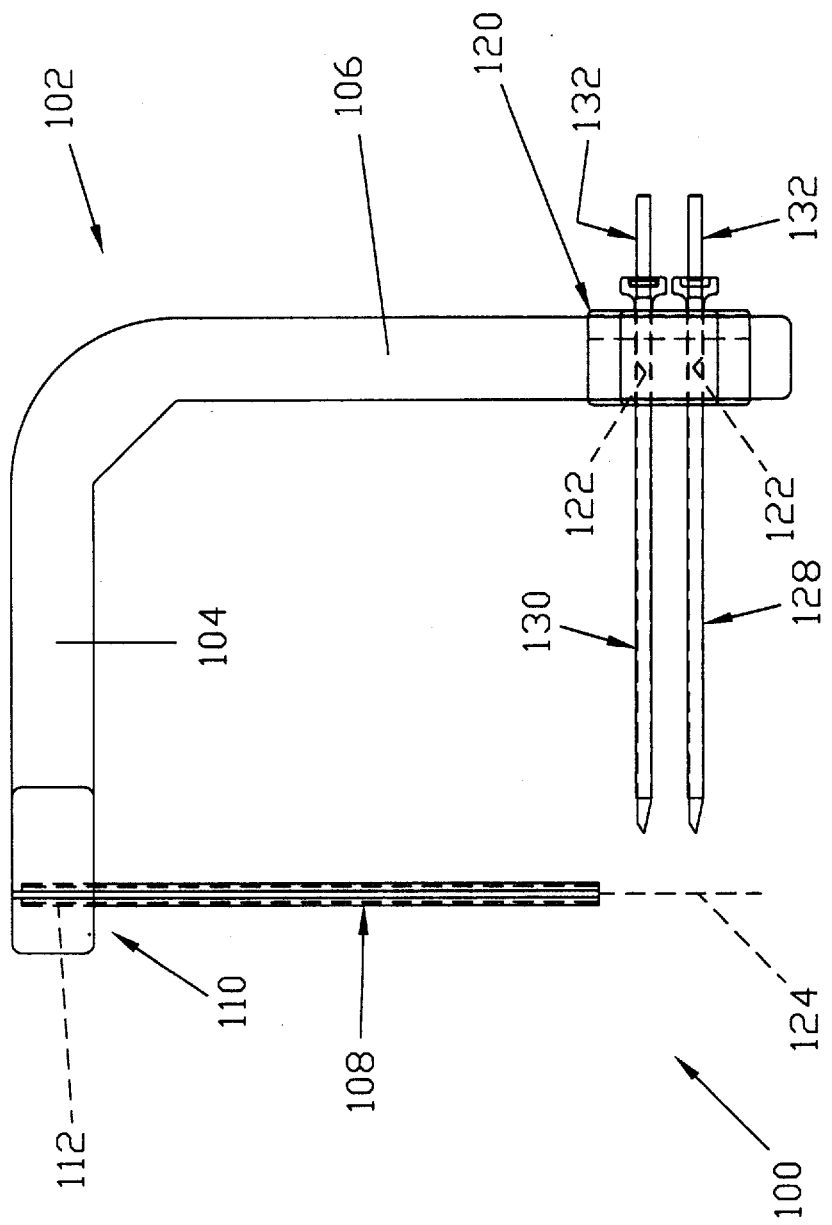
FIG. 29 is a side elevational view of another form of rack assembly illustrative of an alternative embodiment of the invention.
Figure 30:
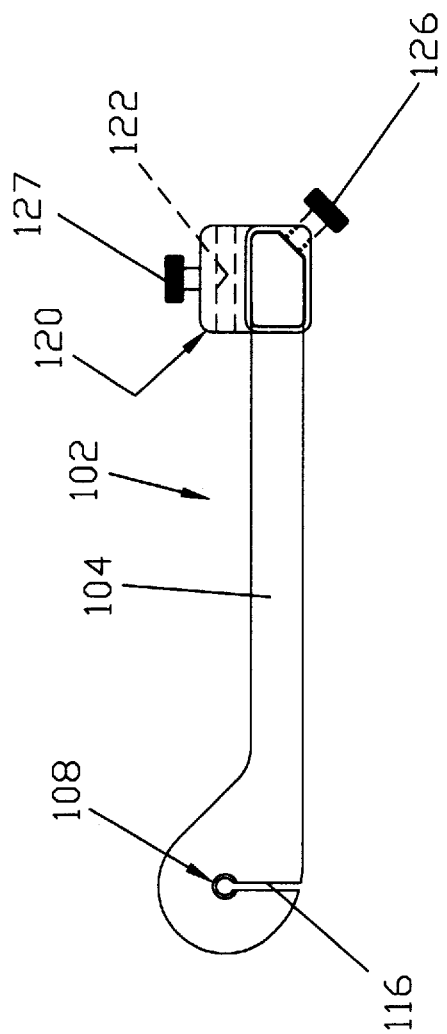
FIG. 30 is a bottom view of the rack assembly of FIG. 29.

Similarly, second absorbable rod 44 is then slid into place through sleeve 76. Sleeve 76 is then removed, leaving second absorbable rod 44, along with first absorbable rod 40, extending through bone block 20 so as to lock bone block 20 in place in femoral tunnel 16, as shown in FIG. 28.

It should be appreciated that it is also possible to provide rack assembly 50 with a guide member 70 which is not formed in two separable halves. In this situation, when the rack's L-shaped member 52 is to be withdrawn from the surgical site (see FIGS. 21 and 22), guide member 70 can simply be detached from L-shaped member 52 by unscrewing set screw 71. Guide member 70 can then be left mounted on the outboard portions of sleeves 74, 76 until sleeves 74, 76 are withdrawn from the surgical site, with guide member 70 being removed with the last of the sleeves 74, 76.

The present invention may also be practiced using the novel rack assembly 100 illustrated in FIGS. 29–33. Rack assembly 100 comprises an L-shaped member 102 having a base portion 104 and an arm portion 106. Arm portion 106 extends transversely of, and preferably is normal to, base portion 104.

Rack assembly 100 also includes a cannulated sleeve 108 which, at a base end 110 thereof, is connected to base portion 104. Cannulated sleeve 108 may be retained in a bore 112 in base portion 104, as by screw threads or a set screw (not shown) or a press fit or the like. Cannulated sleeve 108 is provided with a slot 114 (FIG. 29) extending substantially throughout the length of sleeve 108. Base portion 104 of L-shaped member 102 is also provided with a slot 116 (FIG. 30) which is alignable with the sleeve's slot 114 so as to place the slots 114, 116 in communication with each other.

A trocar sleeve guide member 120 is removably connectable to arm portion 106 of L-shaped member 102. Trocar sleeve guide member 120 is provided with bores 122 extending therethrough. Bores 122 extend substantially normal to a hypothetical extension of the longitudinal axis 124 of cannulated sleeve 108. A set screw 126 (FIG. 30) may be used to releasably retain trocar sleeve guide member 120 in position on arm portion 106. To assist in positioning trocar sleeve guide member 120 on arm portion 106 of L-shaped member 102, arm portion 106 may be provided with a stop means (not shown) for limiting movement of member 120 on arm portion 106. Trocar sleeve guide member 120 is preferably formed in two halves releasably held together by a set screw 127 (FIG. 30), whereby trocar sleeve guide member 120 can be slidably mounted on, or detachable from, trocar sleeves 128, 130 passing through bores 122, as will hereinafter be discussed.

First and second trocar sleeves 128, 130 are received by bores 122, such that sleeves 128, 130 are axially and rotatably movable in bores 122. The two trocar sleeves 128, 130 are substantially identical to the sleeve 74 shown in FIGS. 16 and 17. Rack assembly 100 also includes one or more trocars 132 for disposition in sleeves 128, 130. The trocar 132 is substantially identical to the trocar 82 shown in FIG. 15. The aforementioned first and second absorbable rods 40, 44 are slidable through sleeves 128, 130.

FIGS. 34–40 illustrate how rack assembly 100 may be used to practice the present invention.

Figure 34:
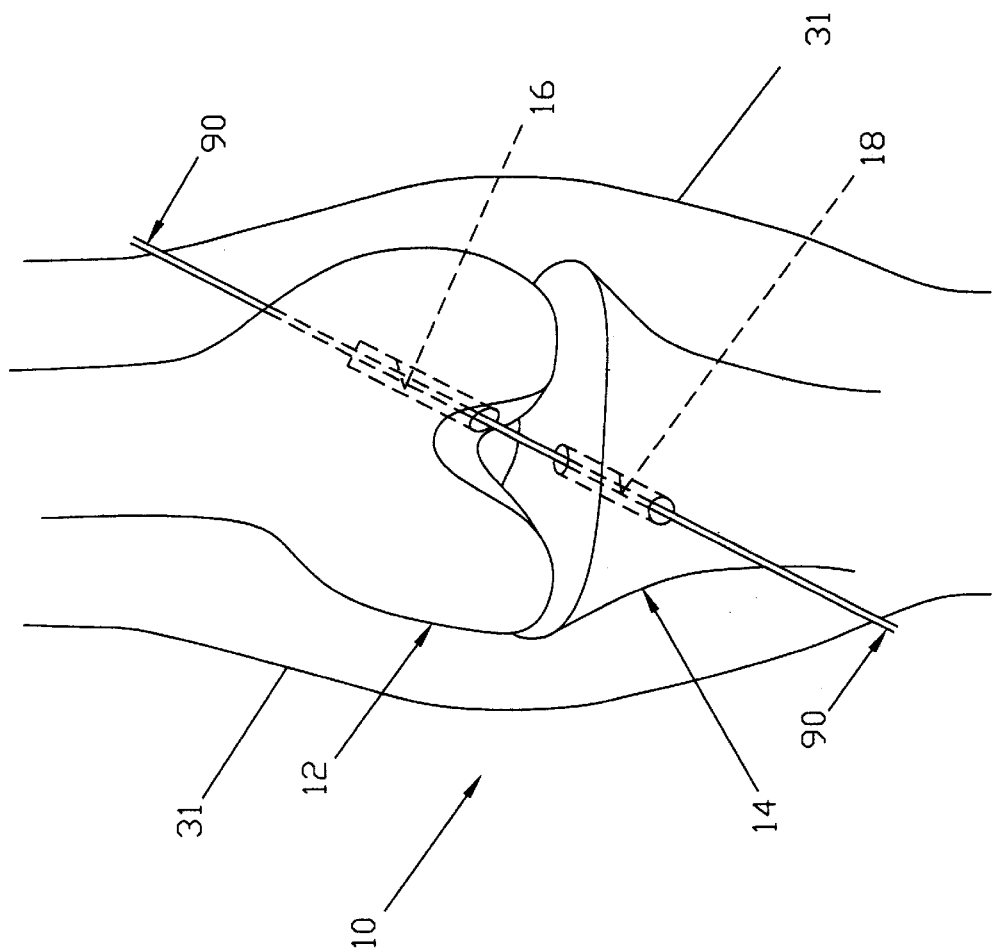
FIG. 34 is a view similar to that of FIG. 18.
Figure 35:
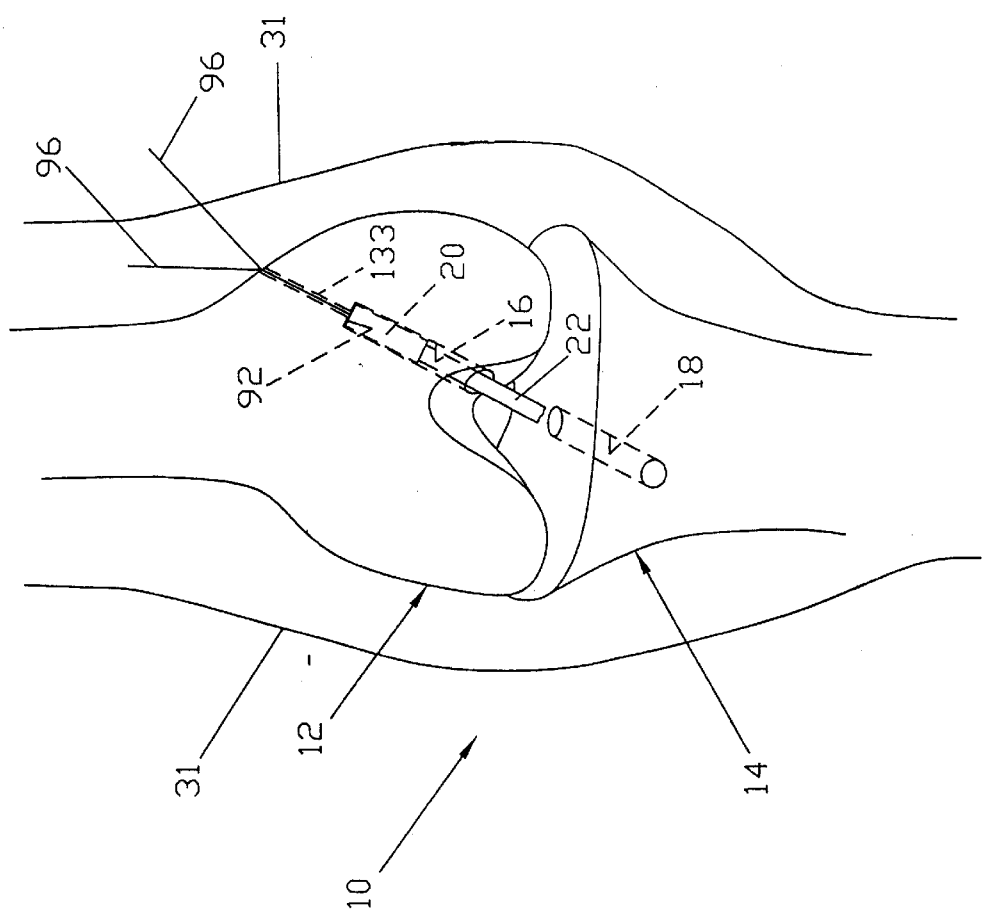
FIGS. 35–40 are diagrammatical views illustrating a series of steps in the use of the rack assembly of FIG. 29.

Referring now to FIG. 34, it will be seen that bone tunnels 16 and 18 are formed in femur 12 and tibia 18, respectively, and a guidewire 90 extends through bone tunnels 16, 18. Guidewire 90 is then used to pull a suture 96, which is attached to bone block 20, up through tibial tunnel 18 and into femoral tunnel 16, such that bone block 20 is in engagement with annular shoulder 92 (FIG. 35). Bone block 20 is kept in this position by maintaining tension on the portion of suture 96 emerging from the top of femur 12.

Figure 36:
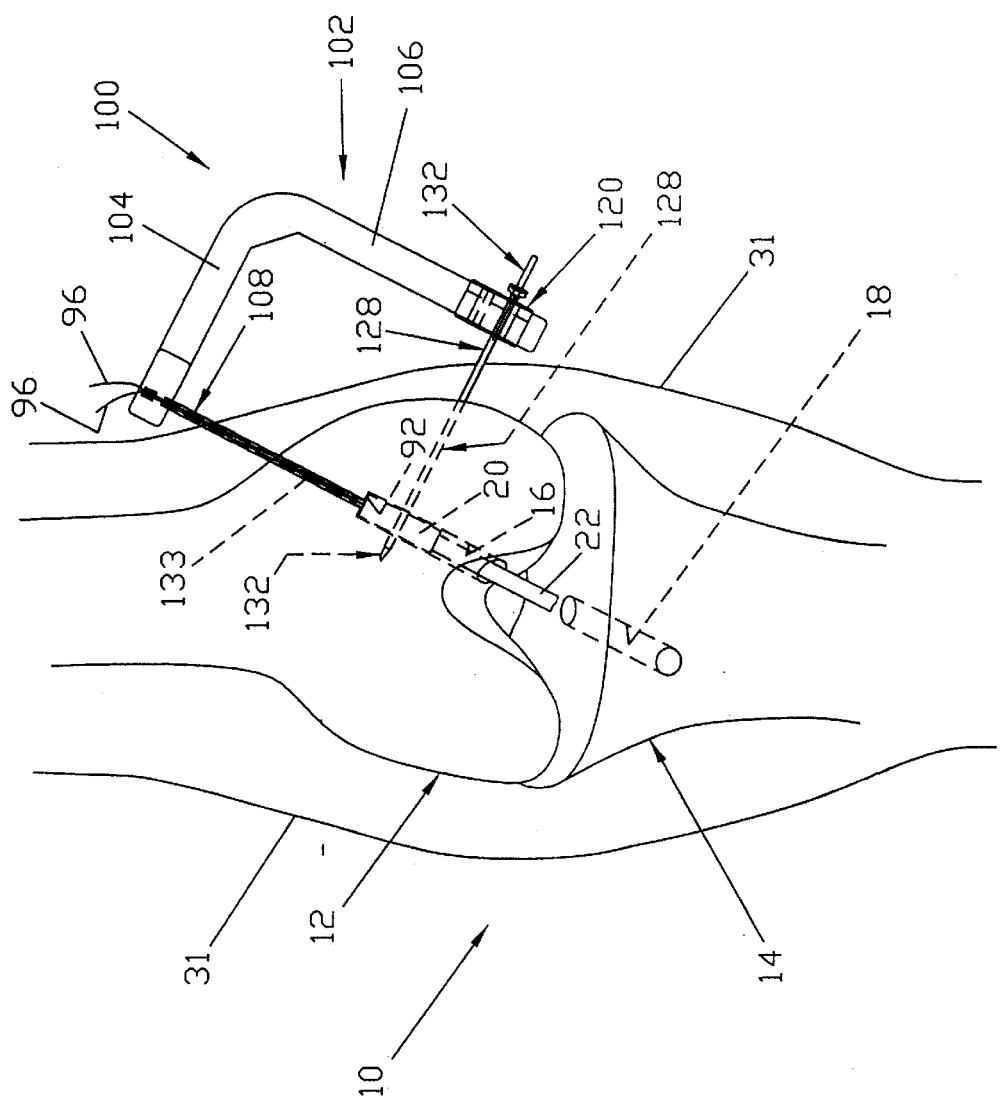
Figure 37:
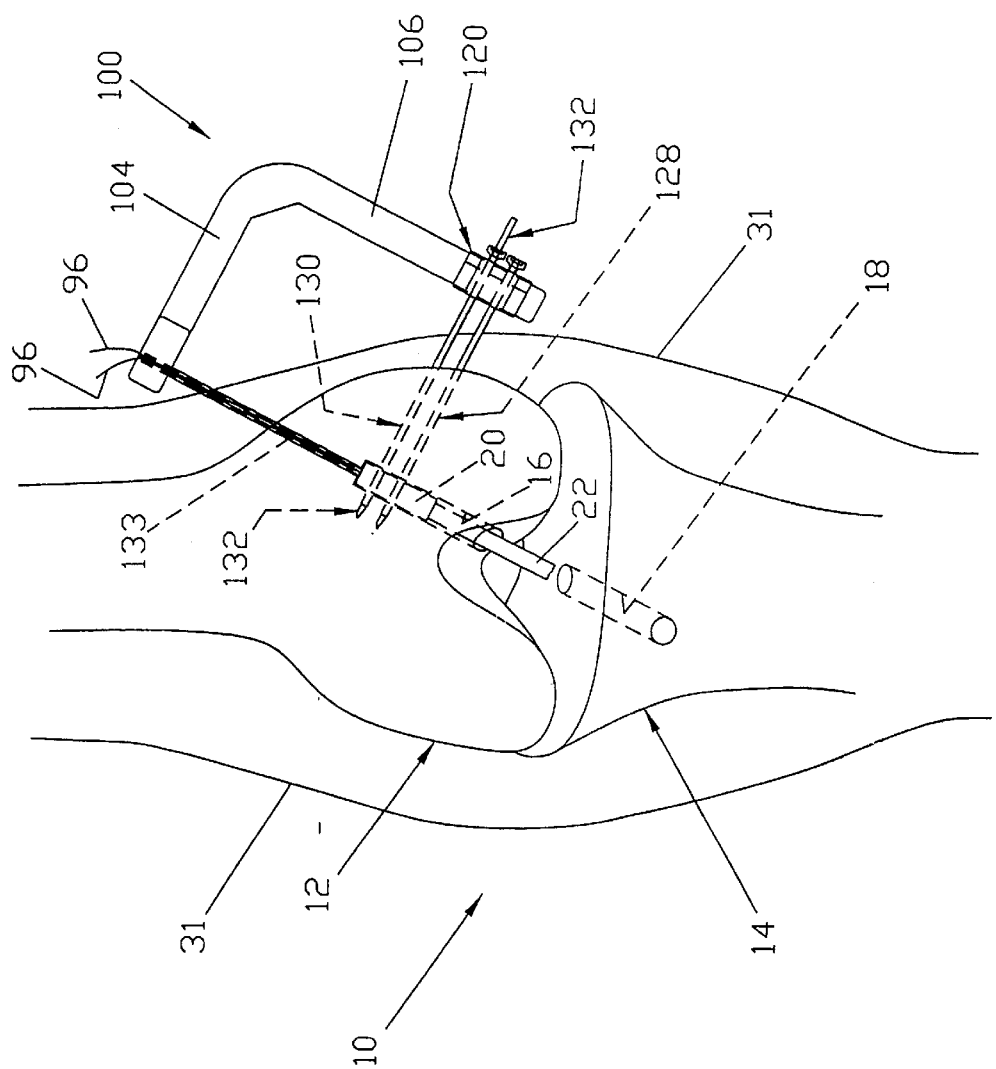

Suture 96 is then introduced into the rack assembly's cannulated sleeve 108 and base portion 104 by way of slots 114, 116. Cannulated sleeve 108 is then passed down the hole 133 (FIGS. 35 and 36) left by the removed guidewire 90 until the distal end of the cannulated sleeve engages the top end of bone block 20 (FIG. 36). Next, first trocar sleeve 128 is extended through a guide member bore 122 and a trocar 132 is inserted into sleeve 128. Alternatively, a trocar 132 may be inserted into first trocar sleeve 128 before first trocar sleeve 128 is inserted into a guide member bore 122. The sleeve 128 and trocar 132 are then drilled, as a unit, into femur 12. With bone block 20 held against shoulder 92 by pulling on suture 96, the combination of sleeve 128 and trocar 132 is drilled through bone block 20 (FIG. 36). In a similar manner, sleeve 130 and trocar 132 (either the same trocar used with sleeve 128 or another trocar) are then drilled through bone block 20, as shown in FIG. 37.

Figure 38:
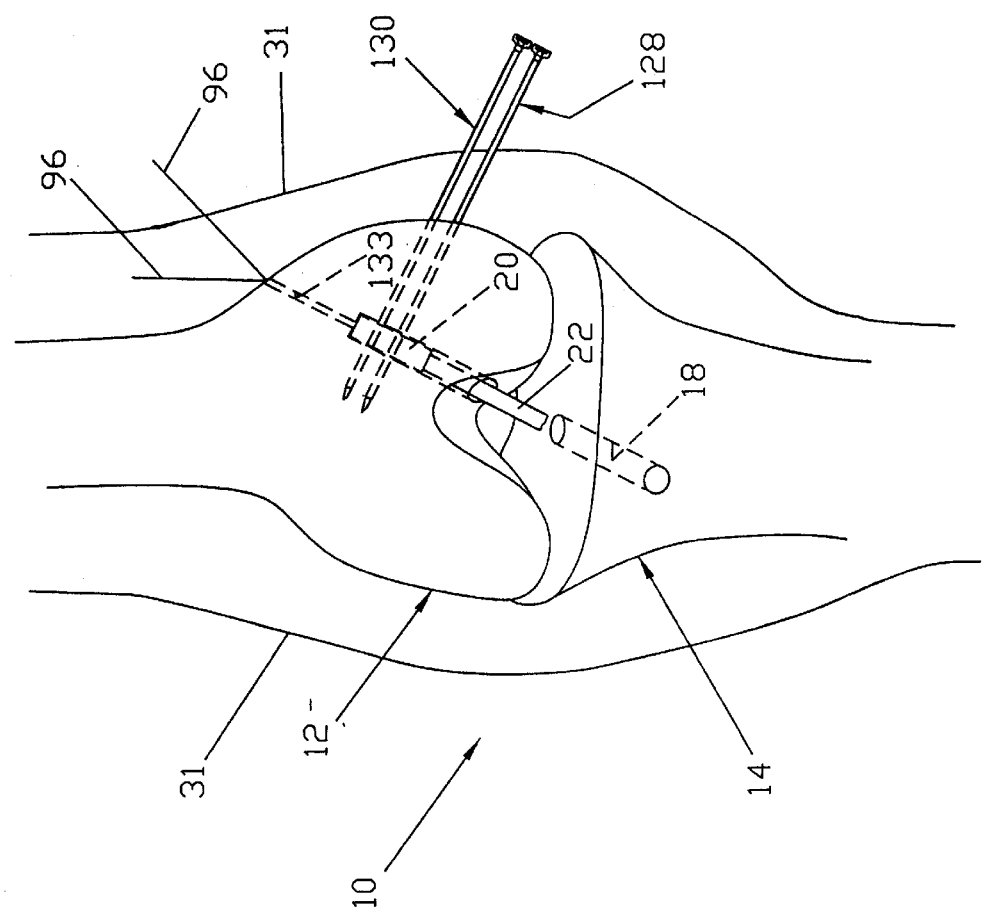
Figure 39:
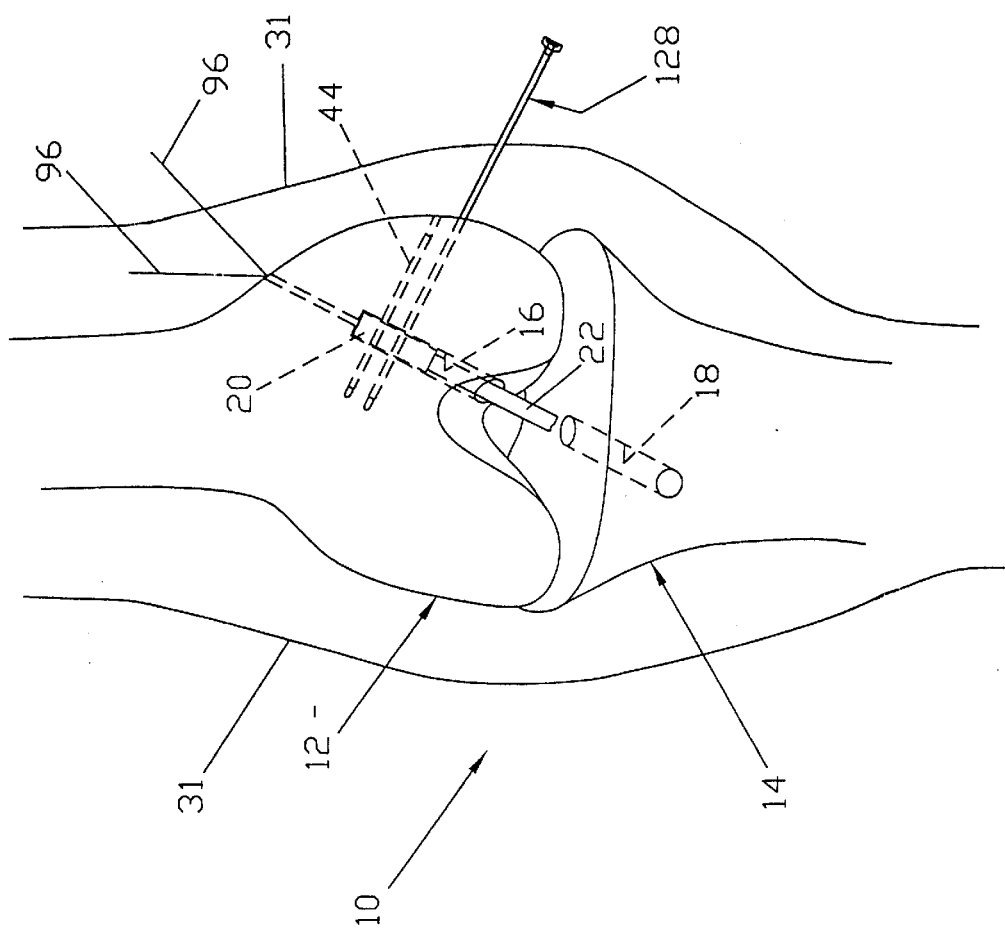
Figure 40:
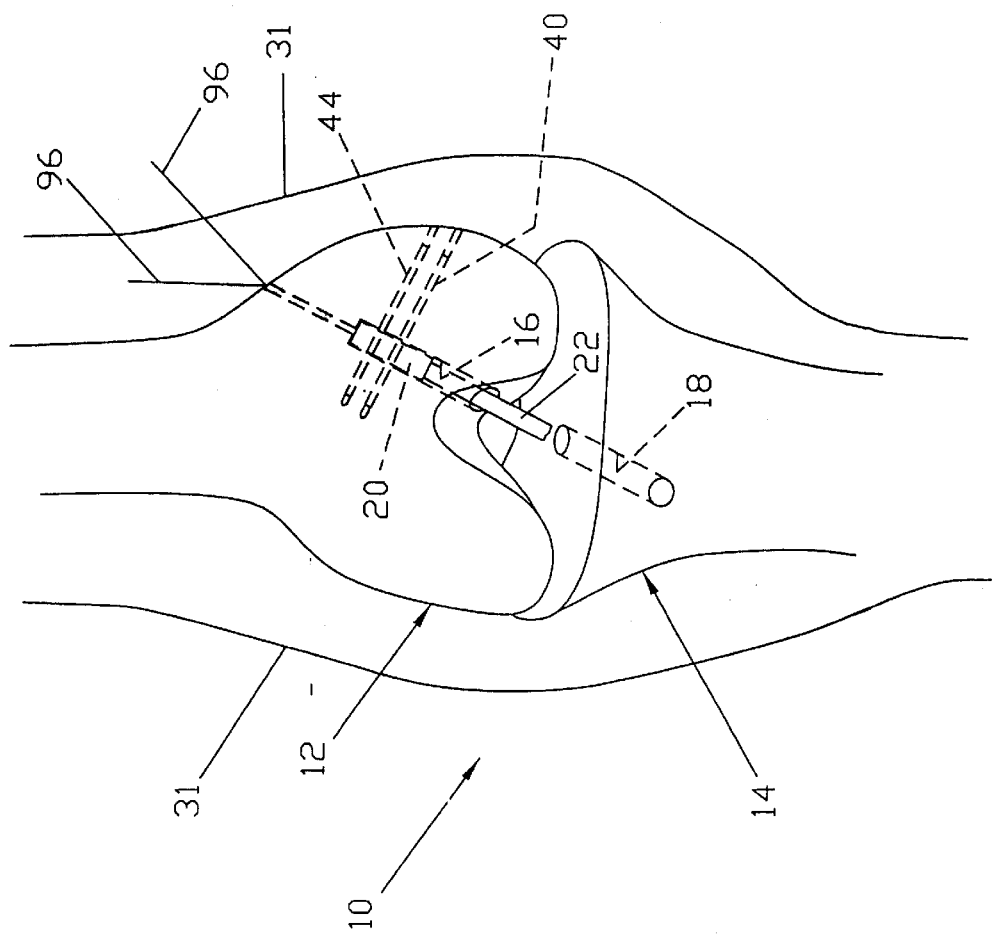

L-shaped member 102 and cannulated sleeve 108 are then removed from the surgical site. This may be accomplished by first loosening set screw 127 (FIG. 30) so as to separate trocar sleeve guide member 120 into its two halves, whereby trocar sleeves 128, 130 will be freed from guide member 120, and then sliding cannulated sleeve 108 upward and out of hole 133. Any trocars 132 are then removed, leaving the trocar sleeves 128, 130 extending into femur 12 and across bone block 20, as shown in FIG. 38.

Second absorbable rod 44 is then slid through sleeve 130 and sleeve 130 removed (FIG. 39), and first absorbable rod 40 is slid through sleeve 128 and sleeve 128 removed, leaving absorbable rods 40, 44 in place (FIG. 40) holding bone block 20 locked in femoral tunnel 16.

Suture 96 is then slipped through bone block 20 and removed, in the manner well known in the art.

It is to be understood that the present invention is by no means limited to the application thereof as herein disclosed and/or as shown in the drawings. For example, for illustrative purposes, the inventive method and apparatus are described herein and illustrated with reference to the human knee joint. It is foreseen that the method and apparatus described herein will be particularly beneficial with respect to such operations. However, it will also be appreciated by those skilled in the art that the method and apparatus described herein find utility with respect to mammals generally, and with respect to other bones as, for example, in shoulder joints or the like.

By way of further example, trocars 82 and 132 and their associated sleeves 74, 76 and 128, 130, respectively, might be passed only part way through bone block 20, but not all the way through; or sleeves 74, 76 and/or sleeves 128, 130 might be stopped short of bone block 20 while trocars 82 and/or 132 penetrate into bone block 20.

Furthermore, trocars 82 and 132 are disclosed herein as being in the form of a hard rod with a sharp tip for penetrating bone. Thus, for example, trocars 82 and 132 might comprise guidewires or K-wires with a pyramidal front point. Alternatively, however, the invention might also be practiced with trocars 82 and 132 comprising a twist drill, a spade drill and/or some other sort of drill.

Also it is contemplated that trocars 82 and/or 132 might be used with their associated rack assemblies 50 and 100, respectively, but without their associated sleeves 74, 76 and 128, 130, respectively. In this case, at least one trocar would always remain positioned in bone block 20 until at least one absorbable rod 40, 44 was positioned in the bone block.

It desired, it is also possible to practice the present invention using just one sleeve 74 and one trocar 82, or just one sleeve 76 and one trocar 82; and it is possible to practice the invention using just one sleeve 128 and one trocar 132, or just one sleeve 130 and one trocar 132. In such a situation, the sleeve element would serve to retain the bone block in position within the bone tunnel while the trocar is replaced by the rod which will ultimately hold the bone block to the bone.

It should also be appreciated that the present application will have utility with respect to setting cross-pins which may not necessarily be absorbable. In particular, the present invention will have utility wherever cross-pinning needs to be achieved for cross-pins which cannot be passed directly through the bone and/or bone block, e.g., where the cross-pins may be too soft or too brittle or too fragile to pass directly through the bone and/or bone block, or where the cross-pins may have a geometry which makes it difficult or impossible for them to be passed directly through the bone and/or bone block. By way of example, the present invention might be used to set cross-pins made out of plastic and/or ceramic materials, or the present invention might be used to set cross-pins made out of metal.

What is claimed is:

1. A method for fixing a bone block in a bone tunnel in a bone, the method comprising the steps of:

placing the bone block in the bone tunnel;

advancing spaced-apart first and second drill means through the bone transversely of the bone tunnel so as to intersect the bone block and extend therethrough;

removing one of the drill means and replacing the one removed drill means with a first absorbable rod; and removing the other of the drill means and replacing the other removed drill means with a second absorbable rod;

whereby to retain the bone block in the bone tunnel with said absorbable rods.

2. A method according to claim 1 wherein said drill means are advanced completely through the bone block.

3. A method according to claim 1 wherein said drill means are advanced partially through the bone block.

4. A method according to claim 1 wherein said drill means comprise drill means selected from a group of drill means consisting of metal wires, twist drills and spade drills.

5. A method for fixing a bone block in a bone tunnel in a bone, the method comprising the steps of:

placing the bone block in the bone tunnel;

advancing a first drill means through a first portion of the bone and transversely of the tunnel so as to intersect and extend through the bone block;

advancing a second drill means through a second portion of the bone and transversely of the tunnel so as to intersect and extend through the bone block, said second drill means being spaced from said first drill means;

removing one of said first and second drill means while leaving the other of said first and second drill means in place in the bone and the bone block;

advancing a first absorbable rod through a bore left by removal of the one drill means, such that the first absorbable rod extends through the bone and the bone block;

removing the other of the first and second drill means; and advancing a second absorbable rod through a bore left by removal of the other drill means, such that the second absorbable rod extends through the bone and the bone block;

whereby to retain the bone block in the bone tunnel with said absorbable rods.

6. A method according to claim 5 wherein said drill means extend completely through the bone block.

7. A method according to claim 5 wherein said drill means extend partially through the bone block.

8. A method according to claim 5 wherein said drill means comprise drill means selected from a group of drill means consisting of metal wires, twist drills and spade drills.

9. A method for fixing a bone block in a bone tunnel in a bone, the method comprising the steps of:

(a) placing the bone block in the bone tunnel;

(b) advancing a plurality of drill means through the bone transversely of the tunnel so as to intercept the bone block and extend therethrough;

(c) removing at least one of the drill means wires while leaving at least one of the drill means in place and replacing the removed at least one drill means with at least one absorbable rod; and (d) removing at least one further of the drill means and replacing the at least one further of the drill means with at least one further absorbable rod; and (e) repeating step (d) until a selected number of the drill means each is replaced by an absorbable rod;

whereby to retain the bone block in the bone tunnel with said absorbable rods.

10. A method for fixing a bone block in a bone tunnel in a bone, the method comprising the steps of:

placing the bone block in the bone tunnel;

advancing spaced-apart first and second trocar and sleeve assemblies through the bone transversely of the bone tunnel so as to intersect the bone block and extend therethrough, the trocar in each of said assemblies being disposed within one of said sleeves of said assemblies and substantially filling said sleeve;

removing said trocar from said first of said sleeves, advancing a first absorbable rod through said first sleeve and through said bone block, and then removing said first sleeve, so as to leave said first absorbable rod in said bone and said bone block; and removing said trocar from said second of said sleeves, advancing a second absorbable rod through said second sleeve and through said bone block, and then removing said second sleeve, so as to leave said second absorbable rod in said bone and said bone block;

whereby to retain the bone block in the bone tunnel with said rods.

11. A method according to claim 10 wherein said trocar comprises only one trocar and said trocar removed from said first of said sleeves is thereafter placed in said second of said sleeves.

12. A method according to claim 10 wherein said first trocar and sleeve assembly comprises a first trocar and said first of said sleeves, and said second trocar and sleeve assembly comprises a second trocar and said second of said sleeves.

13. A method according to claim 10 wherein said trocar and sleeve assemblies extend completely through the bone block.

14. A method according to claim 10 wherein said trocar and sleeve assemblies extend partially through the bone block.

15. A method for fixing a bone block in a bone tunnel in a bone, the method comprising the steps of:

placing the bone block in the bone tunnel;

advancing spaced-apart first and second trocar and sleeve assemblies through the bone transversely of the bone tunnel so as to intersect the bone block and extend therethrough, the trocar in each of said assemblies being disposed within one of said sleeves of said assemblies and substantially filling said sleeve;

removing said trocar from said sleeves;

advancing absorbable rods through said sleeves and through said bone block; and removing said sleeves from said bone block and said bone, so as to leave said absorbable rods in said bone block and said bone;

whereby to retain the bone block in the bone tunnel with said rods.

16. A method for fixing a bone block in a bone tunnel in a bone covered by skin, the method comprising the steps of:

placing the bone block in the bone tunnel;

providing a trocar and sleeve assembly comprising a trocar and a sleeve, wherein said trocar is disposed within said sleeve;

advancing said trocar and sleeve assembly through the skin and through the bone transversely of the bone tunnel such that said trocar and said sleeve intersect the bone block and extend at least partially therethrough;

removing said trocar from said sleeve;

advancing a rod through said sleeve and through the skin and into the bone and into the bone block; and removing said sleeve, to leave the rod in the bone and the bone block to retain the bone block in the bone tunnel.

17. A method for fixing a bone block in a bone tunnel in a bone, the method comprising the steps of:

placing the bone block in the bone tunnel;

advancing spaced-apart first and second trocar and sleeve assemblies through skin covering the bone and through the bone transversely of the bone tunnel so as to intersect the bone block and extend therethrough, the trocar in each of said assemblies being disposed within one of said sleeves of said assemblies and substantially filling said sleeve;

removing said trocar from said first of said sleeves, advancing a first rod through said first sleeve and through said bone block, and then removing said first sleeve, so as to leave said first rod in said bone and said bone block; and removing said trocar from said second of said sleeves, advancing a second rod through said second sleeve and through said bone block, and then removing said second sleeve, so as to leave said second rod in said bone and said bone block;

whereby to retain the bone block in the bone tunnel with said rods.

18. A rack assembly for cross-pinning a bone block in a bone tunnel in a human femur, said rack assembly comprising:

an L-shaped member having a base portion and an arm portion extending transversely of said base portion;

a cannulated sleeve for movement through a tibia and into the femur and for disposition in the bone tunnel, said cannulated sleeve having an enlarged head portion at a free end thereof for disposition in the bone tunnel in the femur and being connectable to the base portion of the L-shaped member at an opposite end thereof;

a trocar sleeve guide member removably connectable to said arm portion of the L-shaped member and having bores extending therethrough at an angle normal to a longitudinal axis of said head portion of said cannulated sleeve;

first and second trocar sleeves for movable disposition in the bores, respectively;

at least one trocar for disposition in said trocar sleeves, the trocar being interconnectable with said trocar sleeve in which the trocar is disposed, said trocar sleeve and said trocar therein being movable axially toward said head portion of said cannulated sleeve and rotatable together such that said interconnected trocar and trocar sleeve are adapted for drilling into the femur and the bone block;

said trocar being removable from said trocar sleeves; and said trocar sleeves being adapted to receive rods slidable through the trocar sleeves and through the bone block, said trocar sleeves being removable from the bone block and the femur and from the rods so as to leave the rods in the bone block and the femur.

19. A rack assembly according to claim 18 wherein said trocar sleeve guide member includes separable first and second parts.

20. A rack assembly according to claim 18 and further comprising said rods.

21. A rack assembly according to claim 20 wherein said rods are of absorbable material.

22. A rack assembly according to claim 18 wherein said trocar guide member bores are aligned with said cannulated sleeve, the axes of said bores being spaced from a plane of said base portion of said L-shaped member.

23. A rack assembly for cross-pinning a bone block in a bone tunnel in a human femur, said rack assembly comprising:

an L-shaped member having a base portion and an arm portion extending transversely of said base portion;

a cannulated sleeve for movement through the femur until a free end thereof is disposed adjacent to the bone block, an opposite end thereof being releasably connectable to said base portion of said L-shaped member;

a trocar sleeve guide member removably connectable to said arm portion of said L-shaped member and having bores extending therethrough at an angle normal to a hypothetical extension of a longitudinal axis of said cannulated sleeve;

first and second trocar sleeves for movable disposition in said bores, respectively;

at least one trocar for movable disposition in said trocar sleeves, said trocar being interconnectable with said trocar sleeve in which said trocar is disposed, said trocar sleeve and said trocar therein being movable axially toward the bone block and rotatable together such that said interconnected trocar and trocar sleeve are adapted for drilling into the femur and the bone block;

said trocar being removable from said trocar sleeves; and absorbable rods for sliding through said trocar sleeves and through said bone block;

said trocar sleeves being removable from the bone block and the femur and from said absorbable rods so as to leave said absorbable rods in the bone block and the femur.

24. A rack assembly according to claim 23 wherein said trocar sleeve guide member includes separable first and second parts.

25. A rack assembly according to claim 23 wherein said cannulated sleeve is provided with a slot extending substantially throughout the length of said cannulated sleeve.

26. A rack assembly according to claim 23 wherein said base portion of said L-shaped member is provided with a slot in communication with said slot of said cannulated sleeve, such that a strand of suture material may be passed widthwise through said slots and into said cannulated sleeve.

* * * * *